United States Patent
Ishii et al.

(10) Patent No.: US 7,741,514 B2
(45) Date of Patent: Jun. 22, 2010

(54) CATALYST COMPRISING N-SUBSTITUTED CYCLIC IMIDE COMPOUND AND PROCESS FOR PRODUCING ORGANIC COMPOUND USING THE CATALYST

(75) Inventors: Yasutaka Ishii, Takatsuki (JP); Tatsuya Nakano, Himeji (JP); Takahiro Iwahama, Himeji (JP); Naruhisa Hirai, Himeji (JP)

(73) Assignee: Daicel Chemical Industries, Ltd., Sakai-shi (JP)

( * ) Notice: Subject to any disclaimer, the term of this patent is extended or adjusted under 35 U.S.C. 154(b) by 0 days.

(21) Appl. No.: 11/504,019

(22) Filed: Aug. 15, 2006

(65) Prior Publication Data

US 2006/0281629 A1   Dec. 14, 2006

Related U.S. Application Data

(62) Division of application No. 10/181,239, filed as application No. PCT/JP01/09767 on Nov. 8, 2001, now Pat. No. 7,115,541.

(30) Foreign Application Priority Data

Nov. 15, 2000  (JP) .............................. 2000-348787
Feb. 22, 2001  (JP) .............................. 2001-046986

(51) Int. Cl.
    *C07C 63/00*    (2006.01)
    *C07C 51/16*    (2006.01)
    *C07C 51/00*    (2006.01)
    *C07D 207/00*   (2006.01)

(52) U.S. Cl. ................. 562/405; 562/415; 562/599; 562/480; 548/402; 548/403

(58) Field of Classification Search ............. 562/480, 562/405, 415, 599; 548/435, 402, 403; 526/259, 526/262
    See application file for complete search history.

(56) References Cited

FOREIGN PATENT DOCUMENTS

| | | |
|---|---|---|
| DE | 135 836 | 10/1902 |
| DE | 112 431 | 4/1975 |
| EP | 0 878 458 A1 | 11/1998 |
| EP | 0 879 812 A1 | 11/1998 |
| EP | 1 004 566 A2 | 5/2000 |
| EP | 1 055 654 A1 | 11/2000 |
| EP | 1 331 215 A1 | 7/2003 |
| JP | 9-87215 A | 3/1997 |
| JP | 10-57814 A | 3/1998 |
| JP | 11-226416 A | 8/1999 |

OTHER PUBLICATIONS

Case, Brenda L., 1998, Texas A and M Univ., College Station, p. 128.
Yoshida et al, Jun. 1996, Wood Res. Inst. meeting, 6th p. 401-404.
Tashiro et al., Adv. Synth. Catal., vol. 343, No. 2, pp. 220-225 (2001).
J.D. Druliner; Polymerization of Acrylates and Methactylates to Make . . . ; Journal of Physical Organic Chemistry, vol. 8, pp. 316-324; 1995.

*Primary Examiner*—Taylor Victor Oh
(74) *Attorney, Agent, or Firm*—Birch, Stewart, Kolasch & Birch, LLP

(57) ABSTRACT

A catalyst of the invention includes an imide compound having a N-substituted cyclic imide skeleton represented by following Formula (I):

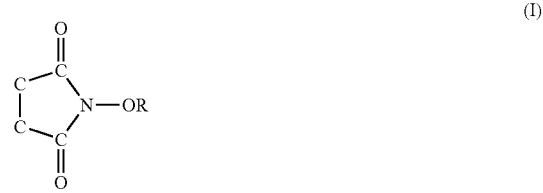

wherein R is a hydroxyl-protecting group. Preferred R is a hydrolyzable protecting group. R may be a group obtained from an acid by eliminating an OH group therefrom. Such acids include, for example, carboxylic acids, sulfonic acids, carbonic acid, carbamic acid, sulfuric acid, nitric acid, phosphoric acids and boric acids. The catalyst may include the imide compound and a metallic compound in combination. In the presence of the catalyst, (A) a compound capable of forming a radical is allowed to react with (B) a radical scavenging compound and thereby yields an addition or substitution reaction product of the compound (A) and the compound (B) or a derivative thereof. This catalyst can produce an organic compound with a high selectivity in a high yield as a result of, for example, an addition or substitution reaction under mild conditions.

3 Claims, No Drawings

US 7,741,514 B2

CATALYST COMPRISING N-SUBSTITUTED CYCLIC IMIDE COMPOUND AND PROCESS FOR PRODUCING ORGANIC COMPOUND USING THE CATALYST

This application is a Divisional of application Ser. No. 10/181,239 filed on Jul. 15, 2002, now U.S. Pat. No. 7,115,541 and for which priority is claimed under 35 U.S.C. §120. Application Ser. No. 10/181,239 is the national phase of PCT International Application No. PCT/JP01/09767 filed on Nov. 8, 2001 under 35 U.S.C. §371. The entire contents of each of the above-identified applications are hereby incorporated by reference. This application also claims priority of Application No. 2000-348787 filed in Japan on Nov. 15, 2000 and Application No. 2001-46986 filed in Japan on Feb. 22, 2001 under 35 U.S.C. §119.

TECHNICAL FIELD

The present invention relates to a catalyst that is useful for oxidation, nitration, carboxylation, reaction for the formation of a carbon-carbon bond, and other reactions and to a process for producing an organic compound using the catalyst.

BACKGROUND ART

An oxidation reaction is one of the most basic reactions in the field of organic chemical industry, and various oxidation processes have been developed. From the viewpoints of resources and environmental issues, a catalytic oxidation process, in which molecular oxygen or air is directly used as an oxidizing agent, is preferred. However, the catalytic oxidation process generally requires high temperatures and/or high pressures for activation of oxygen or, alternatively, must be performed in the co-existence of a reducing agent such as an aldehyde to proceed the reaction under mild conditions. Accordingly, such a conventional catalytic oxidation process cannot easily and efficiently produce an alcohol or a carboxylic acid under mild conditions.

Lower hydrocarbons such as methane and ethane are nitrated using nitric acid or nitrogen dioxide at high temperatures of from 250° C. to 300° C. However, when a hydrocarbon having a large number of carbon atoms is nitrated under the above condition, the substrate is decomposed, and a target nitro compound cannot be obtained in a high yield. To nitrate hydrocarbons, a method using mixed acid (a mixture of nitric acid and sulfuric acid) is widely employed. However, this method requires large amounts of a strong acid in a high concentration.

Additionally, few processes are known for efficiently and directly introducing carboxyl groups into hydrocarbons under mild conditions.

A variety of processes are known for producing organic sulfur acids or salts thereof. For example, processes for producing a sulfonic acid include a process of oxidizing a thiol or disulfide with an oxidizing agent, a process of allowing an aromatic hydrocarbon to react with anhydrous $SO_3$-pyridine or chlorosulfuric acid by using a Friedel-Crafts reaction, and a process of synthetically obtaining a sulfonic acid by subjecting an unsaturated compound to free-radical addition. These processes, however, require extreme reaction conditions or inevitably produce large amounts of by-products. Additionally, no processes for directly and efficiently sulfonating non-aromatic hydrocarbons have been known.

Processes are known in which a variety of compounds are added to unsaturated compounds each having a carbon-carbon double bond or heteroatom-containing compounds and thereby yield useful organic compounds. For example, when an active methylene compound such as a malonic diester is allowed to react with an olefin having an electron attractive group, such as acrylonitrile, in the presence of a base, a carbon-carbon bond is formed as a result of a nucleophilic addition reaction and thereby yields an addition product (Michael addition reaction). When two types of carbonyl compounds are treated in the presence of an acid or a base, one carbonyl compound is nucleophilically added to the other to form a carbon-carbon bond and thereby yields an aldol condensate.

These processes, however, are generally performed in the presence of an acid or base and cannot be applied to compounds each having a substituent that is susceptible to the acid or base. In addition, these processes cannot allow, for example, a hydroxymethyl group, an alkoxymethyl group, an acyl group or a tertiary carbon atom to directly combine with a carbon atom constituting an unsaturated boned of an unsaturated compound or with a methine carbon atom of a bridged cyclic compound.

Addition reactions to a carbon-carbon double bond in accordance with a radical mechanism or coupling reactions to form a carbon-carbon bond are also known. However, there are few processes that can efficiently yield addition or substitution reaction products or derivatives thereof by action of, for example, molecular oxygen under mild conditions.

Some processes are known as production processes of hydroxy-γ-butyrolactone derivatives. For example, European Patent Publication EP-A-2103686 discloses a process for synthetically obtaining pantolactone by allowing glyoxylic acid to react with isobutylene. Likewise, Japanese Unexamined Patent Application Publication No. 61-282373 discloses a process for synthetically obtaining pantolactone by allowing hydrated glyoxylic acid to react with t-butyl alcohol. Tetrahedron, 933 (1979) discloses a process for synthetically obtaining pantolactone. This process includes the steps of hydrolyzing 4-hydroxy-2-methyl-5,5,5-trichloro-1-pentene to yield 2-hydroxy-4-methyl-4-pentenoic acid and cyclizing this compound in the presence of hydrochloric acid. In addition, The Chemical Society of Japan, Spring Conference Proceedings II, pp. 1015 (1998) reports that light irradiation to a mixture solution containing an α-acetoxy-α,β-unsaturated carboxylic ester and 2-propanol yields a corresponding α-acetoxy-γ,γ-dimethyl-γ-butyrolactone derivative. However, each of these processes employs a material that is not easily available or requires special conditions for the reaction.

Japanese Unexamined Patent Application Publications No. 8-38909 and No. 9-327626 each propose an oxidation catalyst comprising an imide compound having a specific structure or the imide compound in combination with, for example, a transition metal compound as a catalyst for oxidizing an organic substrate with molecular oxygen. Japanese Unexamined Patent Application Publication No. 11-239730 discloses a process, in which a substrate is allowed to react with at least one reactant selected from (i) nitrogen oxides and (ii) mixtures of carbon monoxide and oxygen in the presence of the imide compound and thereby at least one functional group selected from nitro group and carboxyl group is introduced into the substrate. PCT International Publication No. WO00/35835 discloses a process, in which two compounds are allowed to react with each other in the presence of a specific imide compound and a radical generator with respect to the imide compound and thereby yield an addition or substitution reaction product or an oxidized product thereof in accordance with a radical mechanism. These processes using the imide compounds can introduce an oxygen-atom-containing group such as hydroxyl group, nitro group or carboxyl group into a substrate or can form a carbon-carbon bond. However, they are still insufficient in yields of the target compounds, stability of the catalysts or amounts of the catalysts.

DISCLOSURE OF INVENTION

Accordingly, an object of the present invention is to provide a catalyst that can yield an organic compound with a high selectivity in a high yield as a result of, for example, an addition or substitution reaction under mild condition and to provide a process for producing an organic compound using the catalyst.

Another object of the present invention is to provide a catalyst that can introduce an oxygen-atom-containing group into an organic substrate under mild conditions and to provide a process for producing an organic compound using the catalyst.

Yet another object of the present invention is to provide a catalyst that is highly stable and can maintain its catalytic activity for a long time.

A further object of the present invention is to provide a radical reaction catalyst that exhibits high catalytic activity even in a small amount.

Another object of the present invention is to provide a radical reaction catalyst that is highly stable even at high temperatures.

After intensive investigations to achieve the above objects, the present inventors have found that, when a compound capable of forming a radical is allowed to react with a radical scavenging compound in the presence of an imide compound having a specific structure, a corresponding addition or substitution reaction product or a derivative thereof can be obtained under mild conditions. The present invention has been accomplished based on these findings.

Specifically, the present invention provides, in an aspect, a catalyst including an imide compound having a N-substituted cyclic imide skeleton represented by following Formula (I):

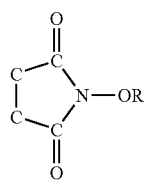

(I)

wherein R is a hydroxyl-protecting group.

Such imide compounds include, for example, a compound represented by following Formula (1):

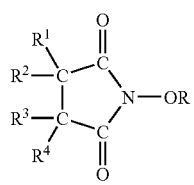

(1)

wherein R is a hydroxyl-protecting group; $R^1$, $R^2$, $R^3$ and $R^4$ are the same or different and are each a hydrogen atom, a halogen atom, an alkyl group, an aryl group, a cycloalkyl group, a hydroxyl group, an alkoxy group, a carboxyl group, a substituted oxycarbonyl group, an acyl group or an acyloxy group, where at least two of $R^1$, $R^2$, $R^3$ and $R^4$ may be combined with each other to form a double bond, an aromatic or non-aromatic ring, and where at least one N-substituted cyclic imido group indicated in Formula (1) may further be formed on $R^1$, $R^2$, $R^3$ and $R^4$ or on the double bond, the aromatic or non-aromatic ring formed by at least two of $R^1$, $R^2$, $R^3$ and $R^4$.

The protecting group R is preferably a hydrolyzable protecting group. R may be a group obtained from an acid by eliminating an OH group from the acid. Such acids include, for example, carboxylic acids, sulfonic acids, carbonic acid, carbamic acid, sulfuric acid, nitric acid, phosphoric acids and boric acids.

The catalyst may include the imide compound and a metallic compound in combination.

In another aspect, the present invention provides a process for producing an organic compound, the process including the step of allowing (A) a compound capable of forming a radical to react with (B) a radical scavenging compound in the presence of the catalyst to yield a product of an addition or substitution reaction between the compound (A) and the compound (B), or a derivative thereof.

As the compound (A) capable of forming a radical, use can be made of one selected from (A1) heteroatom-containing compounds each having a carbon-hydrogen bond at the adjacent position to the heteroatom, (A2) compounds each having a carbon-heteroatom double bond, (A3) compounds each having a methine carbon atom, (A4) compounds each having a carbon-hydrogen bond at the adjacent position to an unsaturated bond, (A5) non-aromatic cyclic hydrocarbons, (A6) conjugated compounds, (A7) amines, (A8) aromatic compounds, (A9) straight-chain alkanes and (A10) olefins.

The radical scavenging compound (B) may be one selected from (B1) unsaturated compounds, (B2) compounds each having a methine carbon atom, (B3) compounds each containing a heteroatom and (B4) oxygen-atom-containing reactants (reacting agents). Such oxygen-atom-containing reactants (B4) include, for example, oxygen, carbon monoxide, nitrogen oxides, sulfur oxides, and nitric acid, nitrous acid or salts thereof.

The reactions between the compound (A) capable of forming a radical and the radical scavenging compound (B) include, for example, oxidation reactions, carboxylation reactions, nitration reactions, sulfonation reactions, coupling reactions and combinations thereof.

The term "addition or substitution" reaction as used herein is used in a broad meaning and also includes, for example, oxidation and sulfonation.

BEST MODE FOR CARRYING OUR THE INVENTION

[Imide Compounds]

A catalyst of the present invention comprises the imide compound having a N-substituted cyclic imide skeleton represented by Formula (I). The imide compound may have a plurality of the N-substituted cyclic imide skeleton represented by Formula (I) in a molecule. The imide compound may also have a plurality of N-oxy cyclic imide skeleton bonded through R, which N-oxy cyclic imide skeleton is obtained from the N-substituted cyclic imide skeleton represented by Formula (I) by eliminating R therefrom.

In Formula (I), the hydroxyl-protecting group represented by R includes conventional protecting groups for a hydroxyl group in the field of organic synthesis. Such protecting groups include, but are not limited to, alkyl groups (e.g., methyl, t-butyl, and other $C_1$-$C_4$ alkyl groups), alkenyl groups (e.g., allyl group), cycloalkyl groups (e.g., cyclohexyl group), aryl groups (e.g., 2,4-dinitrophenyl group), aralkyl groups (e.g., benzyl, 2,6-dichlorobenzyl, 3-bromobenzyl, 2-nitrobenzyl, and triphenylmethyl groups); substituted methyl groups (e.g., methoxymethyl, methylthiomethyl, benzyloxymethyl, t-butoxymethyl, 2-methoxyethoxymethyl, 2,2,2-trichloroethoxymethyl, bis(2-chloroethoxy)methyl, and 2-(trimethylsilyl)ethoxymethyl groups), substituted ethyl groups (e.g., 1-ethoxyethyl, 1-methyl-1-methoxyethyl, 1-isopropoxyethyl, 2,2,2-trichloroethyl, and 2-methoxyethyl groups), tetrahydropyranyl group, tetrahydrofuranyl group, 1-hydroxyalkyl groups (e.g., 1-hydroxyethyl, 1-hydroxyhexyl, 1-hydroxydecyl, 1-hydroxyhexadecyl, and 1-hydroxy-1-phenylmethyl groups), and other groups that can form an acetal group or hemiacetal group with a hydroxyl group; acyl groups (e.g., formyl, acetyl, propionyl, butyryl, isobutyryl, valeryl, pivaloyl, hexanoyl, heptanoyl, octanoyl, nonanoyl, decanoyl, lauroyl, myristoyl, palmitoyl, stearoyl, and-other $C_1$-$C_{20}$ aliphatic acyl groups, and other aliphatic saturated or unsaturated acyl groups; acetoacetyl group; cyclopentanecarbonyl, cyclohexanecarbonyl, and other cycloalkanecarbonyl groups, and other alicyclic acyl groups; benzoyl, naphthoyl, and other aromatic acyl groups), sulfonyl groups (e.g., methanesulfonyl, ethanesulfonyl, trifluoromethanesulfonyl, benzenesulfonyl, p-toluenesulfonyl, and naphthalenesulfonyl groups), alkoxycarbonyl groups (e.g., methoxycarbonyl, ethoxycarbonyl, t-butoxycarbonyl, and other $C_1$-$C_4$ alkoxycarbonyl groups), aralkyloxycarbonyl groups (e.g., benzyloxycarbonyl group and p-methoxybenzyloxycarbonyl group), substituted or unsubstituted carbamoyl groups (e.g., carbamoyl, methylcarbamoyl, and phenylcarbamoyl groups), groups obtained from inorganic acids (e.g., sulfuric acid, nitric acid, phosphoric acids, and boric acids) by eliminating an OH group therefrom, dialkylphosphinothioyl groups (e.g., dimethylphosphinothioyl group), diarylphosphinothioyl groups (e.g., diphenylphosphinothioyl group), and substituted silyl groups (e.g., trimethylsilyl, t-butyldimethylsilyl, tribenzylsilyl, and triphenylsilyl groups).

The imide compound may have a plurality of N-oxy cyclic imide skeleton bonded through R, which N-oxy cyclic imide skeleton is obtained from the N-substituted cyclic imide skeleton represented by Formula (I) by eliminating R therefrom. In this case, R includes, but is not limited to, oxalyl, malonyl, succinyl, glutaryl, adipoyl, phthaloyl, isophthaloyl, terephthaloyl, and other acyl groups derived from polycarboxylic acids; carbonyl group; and methylene, ethylidene, isopropylidene, cyclopentylidene, cyclohexylidene, benzylidene, and other polyvalent hydrocarbon groups (specifically, groups that form acetal bonds with two hydroxyl groups).

The protecting groups other than alkyl groups (e.g., methyl group) are more preferred as R. Specifically preferred Rs include, for example, groups that can form an acetal or hemiacetal with a hydroxyl group; groups (e.g., acyl groups, sulfonyl groups, alkoxycarbonyl groups, and carbamoyl groups) obtained from acids (e.g., carboxylic acids, sulfonic acids, carbonic acid, carbamic acid, sulfuric acid, phosphoric acids, and boric acids) by eliminating an OH group therefrom, and other hydrolyzable protecting groups that can be deprotected by hydrolysis.

Typical examples of the imide compounds are the imide compounds represented by Formula (1). Of the substituents $R^1$, $R^2$, $R^3$ and $R^4$ in the imide compounds, the halogen atom includes iodine, bromine, chlorine and fluorine atoms. The alkyl group includes, but is not limited to, methyl, ethyl, propyl, isopropyl, butyl, isobutyl, s-butyl, t-butyl, hexyl, decyl, and other straight- or branched-chain alkyl groups each having from about 1 to about 10 carbon atoms. Preferred alkyl groups are alkyl groups each having from about 1 to about 6 carbon atoms, of which lower alkyl groups each having from about 1 to 4 carbon atoms are typically preferred.

The aryl group includes phenyl and naphthyl groups, for example. Illustrative cycloalkyl groups are cyclopentyl and cyclohexyl groups. Illustrative alkoxy groups are methoxy, ethoxy, isopropoxy, butoxy, t-butoxy, hexyloxy, and other alkoxy groups each having from about 1 to about 10 carbon atoms, and preferably having from about 1 to about 6 carbon atoms. Among them, lower alkoxy groups each having from about 1 to about 4 carbon atoms are typically preferred.

Examples of the substituted oxycarbonyl group include methoxycarbonyl, ethoxycarbonyl, isopropoxycarbonyl, butoxycarbonyl, t-butoxyparbonyl, hexyloxycarbonyl, heptyloxycarbonyl, octyloxycarbonyl, decyloxycarbonyl, dodecyloxycarbonyl, tetradecyloxycarbonyl, hexadecyloxycarbonyl, octadecyloxycarbonyl, and other alkoxycarbonyl groups (especially, $C_1$-$C_{20}$ alkoxy-carbonyl groups); cyclopentyloxycarbonyl, cyclohexyloxycarbonyl, and other cycloalkyloxycarbonyl groups (especially, 3- to 15-membered cycloalkyloxycarbonyl groups); phenyloxycarbonyl, naphthyloxycarbonyl, and other aryloxycarbonyl groups (especially, $C_6$-$C_{20}$ aryloxy-carbonyl groups); and benzyloxycarbonyl and other aralkyloxycarbonyl groups (especially, $C_7$-$C_2$, aralkyloxy-carbonyl groups).

The acyl group includes, but is not limited to, formyl, acetyl, propionyl, butyryl, isobutyryl, valeryl, pivaloyl, hexanoyl, heptanoyl, octanoyl, nonanoyl, decanoyl, lauroyl, myristoyl, palmitoyl, stearoyl, and other $C_1$-$C_{20}$ aliphatic acyl groups, and other aliphatic saturated or unsaturated acyl groups; acetoacetyl group; cyclopentanecarbonyl, cyclohexanecarbonyl, and other cycloalkanecarbonyl groups and other alicyclic acyl groups; benzoyl, naphthoyl, and other aromatic acyl groups.

The acyloxy group includes, but is not limited to, formyloxy, acetyloxy, propionyloxy, butyryloxy, isobutyryloxy, valeryloxy, pivaloyloxy, hexanoyloxy, heptanoyloxy, octanoyloxy, nonanoyloxy, decanoyloxy, lauroyloxy, myristoyloxy, palmitoyloxy, stearoyloxy, and other $C_1$-$C_{20}$ aliphatic acyloxy groups, and other aliphatic saturated or unsaturated acyloxy groups; acetoacetyloxy group; cyclopentanecarbonyloxy, cyclohexanecarbonyloxy, and other cycloalkanecarbonyloxy groups and other alicyclic acyloxy groups; benzoyloxy, naphthoyloxy, and other aromatic acyloxy groups.

The substituents $R^1$, $R^2$, $R^3$ and $R^4$ may be the same or different. In Formula (1), at least two of $R^1$, $R^2$, $R^3$ and $R^4$ may be combined to form a double bond, an aromatic or non-aromatic ring. The preferred aromatic or non-aromatic ring has from about 5 to about 12 members, and specifically from about 6 to about 10 members. The ring may be a heterocyclic ring or condensed heterocyclic ring, but it is often a hydrocarbon ring. Such rings include, for example, non-aromatic alicyclic rings (e.g., cyclohexane ring and other cycloalkane rings which may have a substituent, cyclohexene ring and other cycloalkene rings which may have a substituent), non-aromatic bridged rings (e.g., 5-norbornene ring and other bridged hydrocarbon rings which may have a substituent), benzene ring, naphthalene ring, and other aromatic rings (including condensed rings) which may have a substituent. The ring comprises an aromatic ring in many cases. The ring may have a substituent. Such substituents include, but are not limited to, alkyl groups, haloalkyl groups, hydroxyl group, alkoxy groups, carboxyl group, substituted oxycarbonyl groups, acyl groups, acyloxy groups, nitro group, cyano group, amino groups, and halogen atoms.

At least one N-substituted cyclic imido group indicated in Formula (1) may further be formed on $R^1$, $R^2$, $R^3$ or $R^4$ or on the double bond or aromatic or non-aromatic ring formed by at least two of $R^1$, $R^2$, $R^3$ and $R^4$. For example, when $R^1$, $R^2$, $R^3$ or $R^4$ is an alkyl group having two or more carbon atoms, the N-substituted cyclic imido group may be formed together with the adjacent two carbon atoms constituting the alkyl group. Likewise, when at least two of $R^1$, $R^2$, $R^3$ and $R^4$ are combined to form a double bond, the N-substituted cyclic imido group may be formed together with the double bond. When at least two of $R^1$, $R^2$, $R^3$ and $R^4$ are combined to form an aromatic or non-aromatic ring, the N-substituted cyclic imido group may be formed with the adjacent two carbon atoms constituting the ring. In addition, a N-hydroxy form (a N-hydroxy cyclic imido group) of the N-substituted cyclic imido group indicated in Formula (1) may be formed on $R^1$, $R^2$, $R^3$ or $R^4$ or on the double bond, aromatic or non-aromatic ring formed by at least two of $R^1$, $R^2$, $R^3$ and $R^4$.

Preferred imide compounds include compounds of the following formulae:

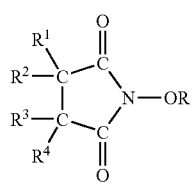
(1a)

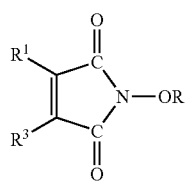
(1b)

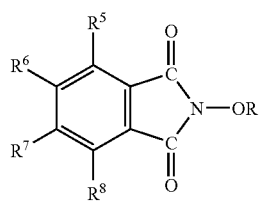
(1c)

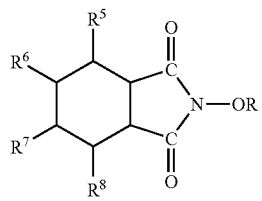
(1d)

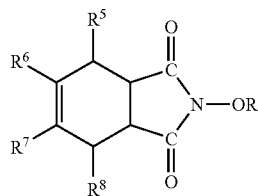
(1e)

-continued

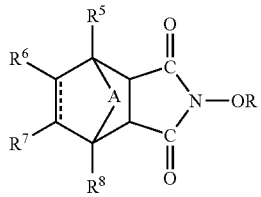
(1f)

wherein $R^5$ to $R^6$ are the same or different and are each a hydrogen atom, an alkyl group, a haloalkyl group, a hydroxyl group, an alkoxy group, a carboxyl group, a substituted oxycarbonyl group, an acyl group, an acyloxy group, a nitro group, a cyano group, an amino group or a halogen atom, where adjacent groups of $R^5$ to $R^8$ may be combined to form an aromatic or non-aromatic ring; A in Formula (1f) is a methylene group or an oxygen atom; and $R^1$, $R^2$, $R^3$, $R^4$ and R have the same meanings as defined above, where one or two of N-substituted cyclic imido group indicated in Formula (1c) or its N-hydroxy form (N-hydroxy cyclic imido group) may further be formed on the benzene ring in Formula (1c).

In the substituents $R^5$ to $R^8$, the alkyl group includes similar alkyl groups to those exemplified above, of which alkyl groups each having from about 1 to about 6 carbon atoms are specifically preferred. The haloalkyl group includes trifluoromethyl group and other haloalkyl groups each having from about 1 to about 4 carbon atoms. The alkoxy group includes similar alkoxy groups to those mentioned above, of which lower alkoxy groups each having from about 1 to about 4 carbon atoms are specifically preferred. The substituted oxycarbonyl group includes similar substituted oxycarbonyl groups (e.g., alkoxycarbonyl groups, cycloalkyloxycarbonyl groups, aryloxycarbonyl groups, and aralkyloxycarbonyl groups) to those described above. The acyl group includes similar acyl groups (e.g., aliphatic saturated or unsaturated acyl groups, acetoacetyl group, alicyclic acyl groups, and aromatic acyl groups) to those described above. The acyloxy group includes similar acyloxy groups (e.g., aliphatic saturated or unsaturated acyloxy groups, acetoacetyloxy group, alicyclic acyloxy groups, and aromatic acyloxy groups) to those mentioned above. The halogen atom includes fluorine, chlorine and bromine atoms. Each of the substituents $R^5$ to $R^8$ is often a hydrogen atom, a lower alkyl group having from about 1 to about 4 carbon atoms, a carboxyl group, a substituted oxycarbonyl group, a nitro group or a halogen atom. The ring formed together by the adjacent groups of $R^5$ to $R^8$ includes similar rings to the aforementioned rings formed by at least two of $R^1$, $R^2$, $R^3$ and $R^4$. Among them, aromatic or non-aromatic 5- to 12-membered rings are specifically preferred.

Examples of the preferred imide compounds are N-acetoxysuccinimide (SP: 26.3), N-acetoxymaleimide (SP: 26.7), N-acetoxyhexahydrophthalimide, N,N'-diacetoxycyclohexanetetracarbodiimide (SP: 28.0), N-acetoxyphthalimide (SP: 27.5), N-acetoxytetrabromophthalimide (SP: 30.3), N-acetoxytetrachlorophthalimide (SP: 31.0), N-acetoxychlorendimide (SP: 28.7), N-acetoxyhimimide (SP: 25.3), N-acetoxytrimellitimide (SP: 30.0), N,N'-diacetoxypyromellitic diimide (SP: 31.1), N,N'-diacetoxynaphthalenetetracarbodiimide (SP: 29.2), N-propionyloxyphthalimide (SP: 26.5), N-butyryloxyphthalimide (SP: 25.8), N-isobutyryloxyphthalimide, N-valeryloxyphthalimide (SP: 25.1), N-pivaloyloxyphthalimide, N-hexanoyloxyphthalimide (SP: 24.1), N-octanoyloxyphthalimide (SP: 23.4), N-decanoyloxyphthalimide (SP: 22.8), N-lauroyloxyphthalimide (SP: 22.3), N-myristoyloxyphthalimide, N-palmitoyloxyphthalimide, N-stearoyloxyphthalimide, N-benzoyloxyphthalimide, and other compounds represented by Formula (1) where R is an acetyl group or another acyl group; N-methoxymethyloxyphthalimide (SP: 25.3), N-(2-methoxyethoxymethyloxy)phthalimide (SP: 24.1), N-tetrahydropyranyloxyphthalimide (SP: 24.7), and other compounds represented by Formula (1) where R is a group that can form an acetal or hemiacetal with a hydroxyl group; N-methanesulfonyloxyphthalimide (SP: 25.9), N-(p-toluenesulfonyloxy)phthalimide (SP: 25.6), and other compounds represented by Formula (1) where R is a sulfonyl group: sulfuric ester (SP: 29.8), nitric ester (SP: 28.5), phosphoric ester (SP: 29.6) or boric ester (SP: 28.6) of N-hydroxyphthalimide, and other compounds represented by Formula (1) where R is a group obtained from an inorganic acid by eliminating an OH group therefrom.

Preferred imide compounds further include, for example, N-acetoxy-α-methylsuccinimide, N-acetoxy-α-ethylsuccinimide, N-acetoxy-α,α-dimethylsuccinimide, N-acetoxy-α,β-dimethylsuccinimide, N-acetoxy-α,α,β,β-tetramethylsuccinimide, and other compounds represented by Formula (1a) where at least one of $R^1$, $R^2$, $R^3$ and $R^4$ is an alkyl group (e.g., a $C_1$-$C_6$ alkyl group), of which compounds where groups of $R^1$, $R^2$, $R^3$ and $R^4$ other than the alkyl group are hydrogen atoms are typically preferred; N,α,β-trisacetoxysuccinimide, N-acetoxy-α,β-bis(propionyloxy)succinimide, N-acetoxy-α,β-bis(butyryloxy)succinimide, N-acetoxy-α,β-bis(isobutyryloxy)succinimide, N-acetoxy-α,β-bis(valeryloxy)succinimide, N-acetoxy-α,β-bis(pivaloyloxy)succinimide, N-acetoxy-α,β-bis(hexanoyloxy)succinimide, N-acetoxy-α,β-bis(octanoyloxy)succinimide, N-acetoxy-α,β-bis(decanoyloxy)succinimide, N-acetoxy-α,β-bis(lauroyloxy)succinimide, N-acetoxy-α,β-bis(myristoyloxy)succinimide, N-acetoxy-α,β-bis(palmitoyloxy)succinimide, N-acetoxy-α,β-bis(stearoyloxy)succinimide, N-acetoxy-α,β-bis(cyclopentanecarbonyloxy)succinimide, N-acetoxy-α,β-bis(cyclohexanecarbonyloxy)succinimide, N-acetoxy-α,β-bis(benzoyloxy)succinimide, and other compounds represented by Formula (1a) where $R^1$ and $R^3$ are acyloxy groups, of which compounds where $R^2$ and $R^4$ are hydrogen atoms are typically preferred; N-acetoxy-4-methoxycarbonylphthalimide (SP: 27.9), N-acetoxy-4-ethoxycarbonylphthalimide (SP: 27.1), N-acetoxy-4-propoxycarbonylphthalimide (SP: 26.4), N-acetoxy-4-isopropoxycarbonylphthalimide, N-acetoxy-4-butoxycarbonylphthalimide (SP: 25.8), N-acetoxy-4-isobutoxycarbonylphthalimide, N-acetoxy-4-t-butoxycarbonylphthalimide, N-acetoxy-4-pentyloxycarbonylphthalimide (SP: 25.3), N-acetoxy-4-hexyloxycarbonylphthalimide (SP: 24.9), N-acetoxy-4-octyloxycarbonylphthalimide (SP: 24.1), N-acetoxy-4-decyloxycarbonylphthalimide (SP: 23.5), N-acetoxy-4-dodecyloxycarbonylphthalimide (SP: 23.0), N-acetoxy-4-tetradecyloxycarbonylphthalimide, N-acetoxy-4-hexadecyloxycarbonylphthalimide, N-acetoxy-4-octadecyloxycarbonylphthalimide, N-acetoxy-4-cyclopentyloxycarbonylphthalimide, N-acetoxy-4-cyclohexyloxycarbonylphthalimide, N-acetoxy-4-phenoxycarbonylphthalimide, N-acetoxy-4-benzyloxycarbonylphthalimide, and other compounds represented by Formula (1c) where R is a substituted oxycarbonyl group; N-acetoxy-4,5-bis(methoxycarbonyl)phthalimide (SP: 28.1), N-acetoxy-4,5-bis(ethoxycarbonyl)phthalimide (SP: 26.8), N-acetoxy-4,5-bis(propoxycarbonyl)phthalimide (SP: 25.8), N-acetoxy-4,5-bis(isopropoxycarbonyl)phthalimide, N-acetoxy-4,5-bis(butoxycarbonyl)phthalimide (SP: 25.0), N-acetoxy-4,5-bis(isobutoxycarbonyl)phthalimide, N-acetoxy-4,5-bis(t-butoxycarbonyl)phthalimide, N-acetoxy-4,5-bis(pentyloxycarbonyl)phthalimide (SP: 24.4), N-acetoxy-4,5-bis(hexyloxycarbonyl)phthalimide (SP: 23.8), N-acetoxy-4,5-bis(octyloxycarbonyl)phthalimide (SP: 22.9), N-acetoxy-4,5-bis(decyloxycarbonyl)phthalimide (SP: 22.3), N-acetoxy-4,5-bis(dodecyloxycarbonyl)phthalimide (SP: 21.8), N-acetoxy-4,5-bis(tetradecyloxycarbonyl)phthalimide, N-acetoxy-4,5-bis(hexadecyloxycarbonyl)phthalimide, N-acetoxy-4,5-bis(octadecyloxycarbonyl)phthalimide, N-acetoxy-4,5-bis(cyclopentyloxycarbonyl)phthalimide, N-acetoxy-4,5-bis(cyclohexyloxycarbonyl)phthalimide, N-acetoxy-4,5-bis(phenoxycarbonyl)phthalimide, N-acetoxy-4,5-bis(benzyloxycarbonyl)phthalimide, and other compounds represented by Formula (1c) where $R^6$ and $R^7$ are substituted oxycarbonyl groups.

Each of the values (SPs) indicated in the parentheses after the names of the aforementioned compounds is a solubility parameter [unit: $(MPa)^{1/2}$] determined by the method of Fedors [R. F. Fedors, Polym. Eng. Sci., 14(2), 147(1974); E. A. Grulke, Polymer Handbook, VII/675; Yuji HARAZAKI, Painting Technology, 3, 129(1987)]. When the catalyst of the present invention is used in a reaction in the absence of a solvent or in a reaction in a nonpolar solvent, imide compounds each having SP of less than or equal to 30 $(MPa)^{1/2}$ and typically of less than or equal to 26 $(MPa)^{1/2}$ are advantageously used, from the viewpoints of solubility of the catalyst in the reaction system, catalytic activity of the catalyst and durability thereof.

Each of the imide compounds can be obtained by introducing a desired protecting group into a corresponding compound where R is a hydrogen atom (N-hydroxy cyclic imide compound) using a conventional reaction for the introduction of a protecting group. For example, N-acetoxyphthalimide can be obtained by allowing N-hydroxyphthalimide to react with acetic anhydride or to react with an acetyl halide in the presence of a base.

The compound where R is a hydrogen atom (N-hydroxy cyclic imide compound) can be obtained by a conventional imidization process (a process for the formation of an imide), such as a process that comprises the steps of allowing a corresponding acid anhydride to react with hydroxylamine for ring-opening of an acid anhydride group, and closing the ring to form an imide.

Typically preferred imide compounds can be obtained by introducing a protecting group into the hydroxyl group of N-hydroxyphthalimide, N,N'-dihydroxypyromelliticdiimide, and other N-hydroxyimide compounds derived from alicyclic polycarboxylic anhydrides or aromatic polycarboxylic anhydrides, specifically those derived from aromatic polycarboxylic anhydrides.

Each of the imide compounds each having the N-substituted cyclic imide skeleton represented by Formula (I) can be used alone or in combination in a reaction. The imide compound may be formed in the reaction system. The imide compound having the N-substituted cyclic imide skeleton represented by Formula (I) can be used in combination with a conventional N-hydroxy cyclic imide compound (a compound where R is a hydrogen atom).

The amount of the imide compound according to the present invention can be selected within a wide range and is, for example, from about 0.0000001 to about 1 mole, preferably from about 0.000001 to about 0.5 mole, more preferably from about 0.00001 to about 0.4 mole, and often from about 0.0001 to about 0.35 mole, relative to 1 mole of a reaction component (substrate).

[Promoter (Co-Catalyst)]

According to the invention, a promoter (co-catalyst) can be used in combination with the imide compound. Such promoters include, for example, metallic compounds. By using the imide compound in combination with the metallic compound, the rate and selectivity of the reaction can be improved.

Metallic elements constituting the metallic compounds are not specifically limited and are often metallic elements of the Groups 2 to 15 of the Periodic Table of Elements. The term "metallic element" as used herein also includes boron B. Examples of the metallic elements include, of the Periodic Table of Elements, Group 2 elements (e.g., Mg, Ca, Sr and Ba), Groups 3 elements (e.g., Sc, lanthanoid elements and actinoid elements), Group 4 elements (e.g., Ti, Zr and Hf), Group 5 elements (e.g., V), Group 6 elements (e.g., Cr, Mo and W), Group 7 elements (e.g., Mn), Group 8 elements (e.g., Fe and Ru), Group 9 elements (e.g., Co and Rh), Group 10 elements (e.g., Ni, Pd and Pt), Group 11 elements (e.g., Cu), Group 12 elements (e.g., Zn), Groups 13 elements (e.g., B, Al and In), Group 14 elements (e.g., Sn and Pb), and Group 15 elements (e.g., Sb and Bi). Preferred metallic elements include transition metal elements (elements of Groups 3 to 12 of the Periodic Table of Elements). Among them, elements of the Groups 5 to 11 of the Periodic Table of Elements are preferred, of which elements of Groups 5 to 9 are typically preferred. Especially, V, Mo, Mn and Co are preferred. The valency of the metallic element is not specifically limited, and is from about 0 to about 6 in many cases.

Such metallic compounds include, but are not limited to, elementary substances, hydroxides, oxides (including complex oxides), halides (fluorides, chlorides, bromides and iodides), salts of oxoacids (e.g., nitrates, sulfates, phosphates, borates, and carbonates), salts of isopolyacids, salts of heteropolyacids, and other inorganic compounds of the aforementioned metallic elements; salts of organic acids (e.g., acetates, propionates, prussiates, naphthenates, or stearates), complexes, and other organic compounds of the metallic elements. Ligands for constituting the complexes include OH (hydroxo), alkoxy (e.g., methoxy, ethoxy, propoxy, and butoxy), acyl (e.g., acetyl and propionyl), alkoxycarbonyl (e.g., methoxycarbonyl and ethoxycarbonyl), acetylacetonato, cyclopentadienyl group, halogen atoms (e.g., chlorine and bromine), CO, CN, oxygen atom, $H_2O$ (aquo), phosphines (triphenylphosphine and other triarylphosphines) and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds.

Specific examples of the metallic compounds include, by taking cobalt compounds as an example, cobalt hydroxide, cobalt oxide, cobalt chloride, cobalt bromide, cobalt nitrate, cobalt sulfate, cobalt phosphate, and other inorganic compounds; cobalt acetate, cobalt naphthenate, cobalt stearate, and other salts of organic acids; acetylacetonatocobalt, and other complexes, and other divalent or trivalent cobalt compounds. Illustrative vanadium compounds include, but are not limited to, vanadium hydroxide, vanadium oxide, vanadium chloride, vanadyl chloride, vanadium sulfate, vanadyl sulfate, sodium vanadate, and other inorganic compounds; acetylacetonatovanadium, vanadyl acetylacetonato, and other complexes, and other vanadium compounds having a valence of from 2 to 5. Examples of compounds of the other metallic elements include compounds corresponding to the abovementioned cobalt or vanadium compounds. Each of these metallic compounds can be used alone or in combination. Specifically, the combination use of a cobalt compound with a manganese compound significantly increases the reaction rate in many cases. The combination use of plural types of metallic compounds having different valances (e.g., a divalent metallic compound in combination with a trivalent metallic compound) is also preferred.

The amount of the metallic compound is, for example, from about 0.001 to about 10 moles and preferably from about 0.005 to about 3 moles, relative to 1 mole of the imide compound, and is, for example, from about 0.00001% by mole to about 10% by mole and preferably from about 0.1% by mole to about 5% by mole, relative to 1 mole of the reaction component (substrate).

The promoters for use in the present invention also include organic salts each composed of a polyatomic cation or a polyatomic anion and its counter ion, which polyatomic cation or anion contains a Group 15 or Group 16 element of the Periodic Table of Elements having at least one organic group bonded thereto. By using the organic salts as the promoters, the rate and selectivity of the reaction can further be improved.

In the organic salts, the Group 15 elements of the Periodic Table of Elements include N, P, As, Sb, and Bi, and the Group 16 elements of the Periodic Table of Elements include, for example, O, S, Se and Te. Preferred elements are N, P, As, Sb and S, of which N, P and S are typically preferred.

The organic groups to be combined with atoms of the elements include, but are not limited to, hydrocarbon groups which may have a substituent, and substituted oxy groups. The hydrocarbon groups include, but are not limited to, methyl, ethyl, propyl, isopropyl, butyl, isobutyl, s-butyl, t-butyl, pentyl, hexyl, octyl, decyl, tetradecyl, hexadecyl, octadecyl, allyl, and other straight-or branched-chain aliphatic hydrocarbon groups (alkyl groups, alkenyl groups and alkynyl groups) each having from about 1 to about 30 carbon atoms (preferably from about 1 to about 20 carbon atoms); cyclopentyl, cyclohexyl, and other alicyclic hydrocarbon groups each having from about 3 to about 8 carbon atoms; and phenyl, naphthyl, and other aromatic hydrocarbon groups each having from about 6 to about 14 carbon atoms. Substituents which the hydrocarbon groups may have include, but are not limited to, halogen atoms, oxo group, hydroxyl group, substituted oxy groups (e.g., alkoxy groups, aryloxy groups, and acyloxy groups), carboxyl group, substituted oxycarbonyl groups, substituted or unsubstituted carbamoyl groups, cyano group, nitro group, substituted or unsubstituted amino groups, alkyl groups (e.g., methyl, ethyl, and other $C_1$-$C_4$ alkyl groups), cycloalkyl groups, aryl groups (e.g., phenyl and naphthyl groups), and heterocyclic groups. The preferred hydrocarbon groups include, for example, alkyl groups each having from about 1 to about 30 carbon atoms, and aromatic hydrocarbon groups (especially, phenyl or naphthyl group) each having from about 6 to about 14 carbon atoms. The substituted oxy groups include, but are not limited to, alkoxy groups, aryloxy groups and aralkyloxy groups.

Examples of the organic salts include organic ammonium salts, organic phosphonium salts, organic sulfonium salts, and other organic onium salts. Such organic ammonium salts include tetramethylammonium chloride, tetraethylammonium chloride, tetrabutylammonium chloride, tetrahexylammonium chloride, trioctylmethylammonium chloride, triethylphenylammonium chloride, tributyl(hexadecyl)ammonium chloride, di(octadecyl)dimethylammonium chloride, and other quaternary ammonium chlorides, and corresponding quaternary ammonium bromides, and other quaternary ammonium salts each having four hydrocarbon groups combined with a nitrogen atom; dimethylpiperidinium chloride, hexadecylpyridinium chloride, methylquinolinium chloride, and other cyclic quaternary ammonium salts. Examples of the organic phosphonium salts include tetramethylphosphonium chloride, tetrabutylphosphonium chloride, tributyl(hexadecyl)phosphonium chloride, triethylphenylphosphonium chloride, and other quaternary phosphonium chlorides, and corresponding quaternary phosphonium bromides, and other quaternary phosphonium salts each having four hydrocarbon groups combined with a phosphorus atom. Examples of the organic sulfonium salts include triethylsulfonium iodide, ethyldiphenylsulfonium iodide, and other sulfonium salts each having three hydrocarbon groups combined with a sulfur atom.

The organic salts also include methanesulfonates, ethanesulfonates, octanesulfonates, dodecanesulfonates, and other alkyl-sulfonates (e.g., $C_6$-$C_{18}$ alkyl-sulfonates); benzenesulfonates, p-toluenesulfonates, naphthalenesulfonates, decylbenzenesulfonates, dodecylbenzenesulfonates, and other aryl-sulfonates which may be substituted with an alkyl group (e.g., $C_6$-$C_{18}$ alkyl-arylsulfonates); sulfonic acid type ion exchange resins (ion exchangers); and phosphonic acid type ion exchange resins (ion exchangers).

The amount of the organic salt is, for example, from about 0.001 to about 0.1 mole and preferably from about 0.005 to about 0.08 mole, relative to 1 mole of the imide compound.

The promoters for use in the present invention also include strong acids (e.g., compounds each having a pKa of less than or equal to 2 at 25° C.). Preferred strong acids include, for example, hydrogen halides, hydrohalogenic acids, sulfuric acid and heteropolyacids. The amount of the strong acid is, for example, from about 0.001 to about 3 moles relative to 1 mole of the imide compound.

The promoters for use in the present invention also include compounds each having a carbonyl group combined with an electron attractive group. Such compounds each having a carbonyl group combined with an electron attractive group include, for example, hexafluoroacetone, trifluoroacetic acid, pentafluorophenyl methyl ketone, pentafluorophenyl trifluoromethyl ketone, and benzoic acid. The amount of this compound is, for example, from about 0.0001 to about 3 moles relative to 1 mole of the reaction component (substrate).

According to the invention, the reaction system may include a radical generator or a radical reaction accelerator. Such components include, but are not limited to, halogens (e.g., chlorine and bromine), peracids (e.g., peracetic acid and m-chloroperbenzoic acid), peroxides (e.g., hydrogen peroxide, t-butyl hydroperoxide (TBHP), and other hydroperoxides), nitric acid, nitrous acid or salts thereof, nitrogen dioxide, benzaldehyde and other aldehydes. The existence of such a component in the system enhances a reaction in some cases. The amount of the aforementioned component is, for example, from about 0.001 to about 3 moles relative to 1 mole of the imide compound.

The catalysts of the present invention are useful as, for example, radical reaction catalysts. The catalysts of the present invention exhibit similar catalytic activities to reactions in which the compounds (N-hydroxy cyclic imide compounds), where a group corresponding to R in Formula (I) is a hydrogen atom, exhibit catalytic activities. In addition, the catalysts of the present invention have significant advantages such that (i) they can maintain the catalytic activities for a long time, (ii) they can exhibit high catalytic activities even in a small amount, and (iii) they can maintain catalytic activities even at high temperatures, as compared with the N-hydroxy cyclic imide compounds. Accordingly, the catalysts of the present invention can be applied to all the reactions, in which the N-hydroxy cyclic imide compounds exhibit catalytic activities, and can yield greater advantages than the case when the N-hydroxy cyclic imide compounds are used as catalysts.

Examples of reactions, in which the catalysts of the present invention exhibit catalytic activities, include reactions described in the following literature relating to the catalytic N-hydroxy cyclic imide compounds: Japanese Unexamined Patent Application Publications No. 8-38909, No. 9-327626, No. 10-286467, No. 10-316610, No. 10-309469, No. 10-316625, No. 11-239730, No. 10-310543, No. 11-49764, No. 11-106377, No. 11-226416, No. 11-228484, No. 11-228481, No. 11-315036, No. 11-300212, No. 11-335304, No. 2000-212116, No. 2000-219650, No. 2000-219652 and No. 2000-256304, PCT International Publications No. WO99/50204, No. WO00/35835, No. WO00/46145 and No. WO00/61665, Japanese Patent Applications No. 11-136339, No. 11-254977, No. 11-372177, No. 2000-648, No. 2000-58054, No. 2000-67682, No. 2000-67679, No. 2000-67680, No. 2000-157356, No. 2000-176494, No. 2000-179185, No. 2000-209205, No. 2000-345822, No. 2000-345823, and No. 2000-345824.

For example, (A) a compound capable of forming a radical is allowed to react with (B) a radical scavenging compound in the presence of the catalyst of the present invention and thereby yields an addition or substitution reaction product between the compound (A) and the compound (B) or a derivative thereof.

[Compounds (A) Capable of Forming Radical]

Such compounds (A) capable of forming a radical are not specifically limited as long as they can form a stable radical and include, for example, (A1) heteroatom-containing compounds each having a carbon-hydrogen bond at the adjacent position to the heteroatom, (A2) compounds each having a carbon-heteroatom double bond, (A3) compounds each having a methine carbon atom, (A4) compounds each having a carbon-hydrogen bond at the adjacent position to an unsaturated bond, (A5) non-aromatic cyclic hydrocarbons, (A6) conjugated compounds, (A7) amines, (A8) aromatic compounds, (A9) straight-chain alkanes and (A10) olefins.

These compounds may have various substituents within a range not adversely affecting the reaction. Such substituents include, but are not limited to, halogen atoms, hydroxyl group, mercapto group, oxo group, substituted oxy groups (e.g., alkoxy groups, aryloxy groups, and acyloxy groups), substituted thio groups, carboxyl group, substituted oxycarbonyl groups, substituted or unsubstituted carbamoyl groups, cyano group, nitro group, substituted or unsubstituted amino groups, sulfo group, alkyl groups, alkenyl group, alkynyl groups, alicyclic hydrocarbon groups, aromatic hydrocarbon groups, and heterocyclic groups.

The compounds (A) capable of forming a radical act as radical donative compounds in the reaction in question.

The heteroatom-containing compounds (A1) each having a carbon-hydrogen bond at the adjacent position to the-heteroatom include, for example, (A1-1) primary or secondary alcohols or primary or secondary thiols, (A1-2) ethers each having a carbon-hydrogen bond at the adjacent position to an oxygen atom, or sulfides each having a carbon-hydrogen bond at the adjacent position to a sulfur atom, (A1-3) acetals (including hemiacetals) each having a carbon-hydrogen bond at the adjacent position to an oxygen atom, or thioacetals (including thiohemiacetals) each having a carbon-hydrogen bond at the adjacent position to a sulfur atom.

The primary or secondary alcohols in the compounds (A1-1) include a wide variety of alcohols. These alcohols may be whichever of monohydric, dihydric and polyhydric alcohols.

Such primary alcohols include, but are not limited to, methanol, ethanol, 1-propanol, 1-butanol, 2-methyl-1-propanol, 1-pentanol, 1-hexanol, 1-octanol, 1-decanol, 1-hexadecanol, 2-buten-1-ol, ethylene glycol, trimethylene glycol, hexamethylene glycol, pentaerythritol, and other saturated or unsaturated aliphatic primary alcohols each having from about 1 to about 30 (preferably from about 1 to about 20, and more preferably from about 1 to about 15) carbon atoms; cyclopentylmethyl alcohol, cyclohexylmethyl alcohol, 2-cyclohexylethyl alcohol, and other saturated or unsaturated alicyclic primary alcohols; benzyl alcohol, 2-phenylethyl alcohol, 3-phenylpropyl alcohol, cinnamyl alcohol, and other aromatic primary alcohols; and 2-hydroxymethylpyridine, and other heterocyclic alcohols.

Typical secondary alcohols include, but are not limited to, 2-propanol, s-butyl alcohol, 2-pentanol, 3-pentanol, 3,3-dimethyl-2-butanol, 2-octanol, 4-decanol, 2-hexadecanol, 2-penten-4-ol, 1,2-propanediol, 2,3-butanediol, 2,3-pentanediol, and other vicinal diols, and other saturated or unsaturated aliphatic secondary alcohols each having from about 3 to about 30 (preferably from about 3 to about 20, and more preferably from about 3 to about 15) carbon atoms; 1-cyclopentylethanol, 1-cyclohexylethanol, and other secondary alcohols each having an aliphatic hydrocarbon group and an alicyclic hydrocarbon (e.g., a cycloalkyl group) combined with a carbon atom that is combined with a hydroxyl group; cyclobutanol, cyclopentanol, cyclohexanol, cyclooctanol, cyclododecanol, 2-cyclohexen-1-ol, 2-adamantanol, 2-adamantanols each having from one to four hydroxyl groups at the bridgehead positions, 2-adamantanols each having an oxo group on an adamantane ring, and other saturated or unsaturated alicyclic secondary alcohols (including bridged cyclic secondary alcohols) each having from about 3 to about 20 members (preferably from about 3 to about 15 members, more preferably from about 5 to about 15 members, and typically from about 5 to about 8 members); 1-phenylethanol, 1-phenylpropanol, 1-phenylmethylethanol, diphenylmethanol, and other aromatic secondary alcohols; and 1-(2-pyridyl)ethanol, and other heterocyclic secondary alcohols.

Typical alcohols further include, for example, 1-adamantanemethanol, α-methyl-1-adamantanemethanol, α-ethyl-1-adamantanemethanol, α-isopropyl-1-adamantanemethanol, 3-hydroxy-α-methyl-1-adamantanemethanol, 3-carboxy-α-methyl-1-adamantanemethanol, α-methyl-3a-perhydroindenemethanol, α-methyl-4a-decalinmethanol, 8a-hydroxy-α-methyl-4a-decalinmethanol, α-methyl-4a-perhydrofluorenemethanol, α-methyl-4a-perhydroanthracenemethanol, α-methyl-8a-perhydrophenanthrenemethanol, α-methyl-2-tricyclo[5.2.1.0$^{2,6}$]decanemethanol, 6-hydroxy-α-methyl-2-tricyclo[5.2.1.0$^{2,6}$]decanemethanol, α-methyl-2a-perhydroacenaphthenemethanol, α-methyl-3a-perhydrophenalenemethanol, α-methyl-1-norbornanemethanol, α-methyl-2-norbornene-1-methanol, and other alcohols each having a bridged cyclic hydrocarbon group, such as compounds each having a bridged cyclic hydrocarbon group combined with a carbon atom that is combined with a hydroxyl group.

Preferred alcohols include secondary alcohols and the alcohols each having a bridged cyclic hydrocarbon group. Such preferred secondary alcohols include 2-propanol, s-butyl alcohol, and other aliphatic secondary alcohols; 1-cyclohexyl ethanol, and other secondary alcohols each having an aliphatic hydrocarbon group (e.g., a $C_1$-$C_4$ alkyl group or a $C_6$-$C_{14}$ aryl group) and a non-aromatic carbocyclic group (e.g., a $C_3$-$C_{15}$ cycloalkyl group or a cycloalkenyl group) combined with a carbon atom that is combined with a hydroxyl group; cyclopentanol, cyclohexanol, 2-adamantanol, and other alicyclic secondary alcohols each having from about 3 to 5 members; 1-phenylethanol, and other aromatic secondary alcohols.

The primary or secondary thiols in the compounds (A1-1) include thiols corresponding to the primary or secondary alcohols.

The ethers each having a carbon-hydrogen bond at the adjacent position to an oxygen atom in the compounds (A1-2) include, but are not limited to, dimethyl ether, diethyl ether, dipropyl ether, diisopropyl ether, dibutyl ether, methyl ethyl ether, methyl butyl ether, ethyl butyl ether, diallyl ether, methyl vinyl ether, ethyl allyl ether, and other aliphatic ethers; anisole, phenetole, dibenzyl ether, phenylbenzyl ether, and other aromatic ethers; and dihydrofuran, tetrahydrofuran, pyran, dihydropyran, tetrahydropyran, morpholine, chroman, isochroman, and other cyclic ethers to which an aromatic or non-aromatic ring may be condensed.

The sulfides each having a carbon-hydrogen bond at the adjacent position to a sulfur atom in the compounds (A1-2) include sulfides corresponding to the ethers each having a carbon-hydrogen bond at the adjacent position to an oxygen atom.

The acetals each having a carbon-hydrogen bond at the adjacent position to an oxygen atom in the compounds (A1-3) include, for example, acetals derived from aldehydes and alcohols or acid-anhydrides. Such acetals include cyclic acetals and acyclic acetals. The aldehydes include, but are not limited to, formaldehyde, acetaldehyde, propionaldehyde, butyraldehyde, isobutyraldehyde, pentanal, hexanal, decanal, and other aliphatic aldehydes; cyclopentanecarbaldehyde, cyclohexanecarbaldehyde, and other alicyclic aldehydes; benzaldehyde, phenylacetaldehyde, and other aromatic aldehydes. The alcohols include, but are not limited to, methanol, ethanol, 1-propanol, 1-butanol, benzyl alcohol, and other monohydric alcohols; ethylene glycol, propylene glycol, 1,3-propanediol, 2,2-dibromo-1,3-propanediol, and other dihydric alcohols. Typical acetals are, for example, 1,3-dioxolane, 2-methyl-1,3-dioxolane, 2-ethyl-1,3-dioxolane, and other 1,3-dioxolane compounds; 2-methyl-1,3-dioxane, and other 1,3-dioxane compounds; acetaldehyde dimethyl acetal, and other dialkyl acetal compounds.

The thioacetals each having a carbon-hydrogen bond at the adjacent position to a sulfur atom in the compounds (A1-3) include thioacetals corresponding to the acetals each having a carbon-hydrogen bond at the adjacent position to an oxygen atom.

The compounds (A2) each having a carbon-heteroatom double bond include, for example, (A2-1) compounds each containing a carbonyl group, (A2-2) compounds each containing a thiocarbonyl group, and (A2-3) imines. The compounds (A2-1) each containing a carbonyl group include ketones and aldehydes. Such ketones and aldehydes include, but are not limited to, acetone, methyl ethyl ketone, methyl isopropyl ketone, methyl isobutyl ketone, methyl s-butyl ketone, methyl t-butyl ketone, 3-pentanone, methyl decyl ketone, methyl isopropyl ketone, isopropyl butyl ketone, methyl vinyl ketone, methyl isopropenyl ketone, methyl cyclohexyl ketone, acetophenone, methyl 2-methylphenyl ketone, methyl 2-pyridyl ketone, cyclohexyl phenyl ketone, and other chain ketones; cyclopropanone, cyclobutanone, cyclopentanone, cyclohexanone, 4-methylcyclohexanone, 4-chlorocyclohexanone, isophorone, cycloheptanone, cyclooctanone, cyclodecanone, cyclododecanone, cyclopentadecanone, 1,3-cyclohexanedione, 1,4-cyclohexanedione, 1,4-cyclooctanedione, 2,2-bis(4-oxocyclohexyl)propane, bis(4-oxocyclohexyl)methane, 4-(4-oxocyclohexyl)cyclohexanone, 2-adamantanone, and other cyclic ketones; biacetyl (2,3-butanedione), 2,3-pentanedione, 3,4-hexanedione, bibenzoyl (benzil), acetylbenzoyl, cyclopentane-1,2-dione, cyclohexane-1,2-dione, and other 1,2-dicarbonyl compounds (e.g., α-diketones); acetoin, benzoin, and other α-keto-alcohols; acetaldehyde, propionaldehyde, butanal, hexanal, succinaldehyde, glutaraldehyde, adipaldehyde, and other aliphatic aldehydes; cyclohexyl aldehyde, citral, citronellal, and other alicyclic aldehydes; benzaldehyde, carboxybenzaldehyde, nitrobenzaldehyde, cinnamaldehyde, salicylaldehyde, anisaldehyde, phthalaldehyde, isophthalaldehyde, terephthalaldehyde, and other aromatic aldehydes; and furfural, nicotinaldehyde, and other heterocyclic aldehydes.

The compounds (A2-2) each having a thiocarbonyl group include compounds each having a thiocarbonyl group corresponding to the compounds (A2-1) each having a carbonyl group.

The imines (A2-3) include, but are not limited to, imines (including oximes and hydrazones) derived from the compounds (A2-1) each having a carbonyl group with ammonia or amines. Such amines include, for example, methylamine, ethylamine, propylamine, butylamine, hexylamine, benzylamine, cyclohexylamine, aniline, and other amines; hydroxylamine, O-methylhydroxylamine and other hydroxylamines; hydrazine, methylhydrazine, phenylhydrazine, and other hydrazines.

The compounds (A3) each having a methine carbon atom include, for example, (A3-1) cyclic compounds each having a methine group (i.e., a methine carbon-hydrogen bond) as a constitutional unit of a ring, and (A3-2) chain compounds each having a methine carbon atom.

The cyclic compounds (A3-1) include, for example, (A3-1a) bridged cyclic compounds each having at least one methine group, and (A3-1b) non-aromatic cyclic compounds (e.g., alicyclic hydrocarbons) each having a hydrocarbon group combined with a ring. The bridged-cyclic compounds also include compounds, in which two rings commonly possess two carbon atoms, such as hydrogenated products of condensed polycyclic aromatic hydrocarbons.

The bridged cyclic compounds (A3-1a) include, but are not limited to, decalin, bicyclo[2.2.0]hexane, bicyclo[2.2.2]octane, bicyclo[3.2.1]octane, bicyclo[4.3.2]undecane, bicyclo [3.3.3]undecane, thujone, carane, pinane, pinene, bornane, bornylene, norbornane, norbornene, camphor, camphoric acid, camphene, tricyclene, tricyclo[5.2.1.0$^{3,8}$]decane, tricyclo[4.2.1.1$^{2,5}$]decane, exotricyclo[5.2.1.0$^{2,6}$]decane, endotricyclo[5.2.1.0$^{2,6}$]decane, tricyclo[4.3.1.1$^{2,5}$]undecane, tricyclo[4.2.2.1$^{2,5}$]undecane, endotricyclo[5.2.2.0$^{2,6}$]undecane, adamantane, 1-adamantanol, 1-chloroadamantane, 1-methyladamantane, 1,3-dimethyladamantane, 1-methoxyadamantane, 1-carboxyadamantane, 1-methoxycarbonyladamantane, 1-nitroadamantane, tetracyclo[4.4.0.1$^{2,5}$1.$^{7,10}$] dodecane, perhydroanthracene, perhydroacenaphthene, perhydrophenanthrene, perhydrophenalene, perhydroindene, quinuclidine, and other bridged cyclic hydrocarbons or bridged heterocyclic compounds each having two to four rings, and derivatives thereof. These bridged cyclic compounds each have a methine carbon atom at a bridgehead position (corresponding to a junction position when two rings commonly possess two atoms).

The non-aromatic cyclic compounds (A3-1b) each having a hydrocarbon group combined with a ring include, but are not limited to, 1-methylcyclopentane, 1-methylcyclohexane, limonene, menthene, menthol, carbomenthone, menthone, and other alicyclic hydrocarbons each having from about 3 to about 15 members and having a hydrocarbon group (e.g., an alkyl group) combined with its ring, and their derivatives. The hydrocarbon group just mentioned above contains from about 1 to about 20 (preferably from about 1 to about 10) carbon atoms. The non-aromatic cyclic compounds (A3-1b) each having a hydrocarbon group combined with a ring have a methine carbon atom at the bonding position between the ring and the hydrocarbon group.

The chain compounds (A3-2) each having a methine carbon atom include, but are not limited to, chain hydrocarbons each having a tertiary carbon atom, such as isobutane, isopentane, isohexane, 3-methylpentane, 2,3-dimethylbutane, 2-methylhexane, 3-methylhexane, 3,4-dimethylhexane, 3-methyloctane, and other aliphatic hydrocarbons each having from about 4 to about 20 (preferably from about 4 to about 10) carbon atoms, and derivatives thereof.

The compounds (A4) each having a carbon-hydrogen bond at the adjacent position to an unsaturated bond include, for example, aromatic compounds each having a methyl group or methylene group at the adjacent position to an aromatic ring (a "benzyl position"), and (A4-2) non-aromatic compounds each having a methyl group or methylene group at the adjacent position to an unsaturated bond (e.g., a carbon-carbon triple bond or a carbon-oxygen double bond).

In the aromatic compounds (A4-1), the aromatic ring may be either of an aromatic hydrocarbon ring or an aromatic heterocyclic ring. Such aromatic hydrocarbon rings include, but are not limited to, benzene ring, condensed carbocyclic rings (e.g., naphthalene, azulene, indacene, anthracene, phenanthrene, triphenylene, pyrene, and other condensed carbocyclic rings in which two to ten 4- to 7-membered carbocyclic rings are condensed). The aromatic heterocyclic rings include, but are not limited to, heterocyclic rings each containing an oxygen atom as a heteroatom (e.g., furan, oxazole, isoxazole and other 5-membered rings; 4-oxo-4H-pyran and other 6-membered rings; benzofuran, isobenzofuran, 4-oxo-4H-chromene and other condensed rings), heterocyclic rings each containing a sulfur atom as a heteroatom (e.g., thiophene, thiazole, isothiazole, thiadiazole, and other 5-membered rings; 4-oxo-4H-thiopyran and other 6-membered rings; benzothiophene and other condensed rings), heterocyclic rings each containing a nitrogen atom as a heteroatom (e.g., pyrrole, pyrazole, imidazole, triazole, and other 5-membered rings; pyridine, pyridazine, pyrimidine, pyrazine, and other 6-membered rings; indole, quinoline, acridine, naphthyridine, quinazoline, purine, and other condensed rings).

The methylene group at the adjacent position to the aromatic ring may be a methylene group constituting a non-aromatic ring condensed to the aromatic ring. In the aromatic compounds (A4-1), both methyl group and methylene group may exist at the adjacent position to the aromatic ring.

The aromatic compounds each having a methyl group at the adjacent position to an aromatic ring include, but are not limited to, aromatic hydrocarbons each having from about one to about six methyl groups substituted on the aromatic ring (e.g., toluene, xylene, 1-ethyl-4-methylbenzene, 1-ethyl-3-methylbenzene, 1-isopropyl-4-methylbenzene, 1-t-butyl-4-methylbenzene, 1-methoxy-4-methylbenzene, mesitylene, pseudocumene, durene, methylnaphthalene, dimethylnaphthalene, methylanthracene, 4,4'-dimethylbiphenyl, tolualdehyde, dimethylbenzaldehyde, trimethylbenzaldehyde, toluic acid, trimethylbenzoic acid, and dimethylbenzoic acid), and heterocyclic compounds each having from about one to about six methyl groups substituted on a heterocyclic ring (e.g., 2-methylfuran, 3-methylfuran, 3-methythiophene, 2-methylpyridine, 3-methylpyridine, 4-methylpyridine, 2,4-dimethylpyridine, 2,4,6-trimethylpyridine, 4-methylindole, 2-methylquinoline, and 3-methylquinoline).

The aromatic compounds each having a methylene group at the adjacent position to an aromatic ring include, but are not limited to, aromatic hydrocarbons each having an alkyl group or substituted alkyl group having two or more carbon atoms (e.g., ethylbenzene, propylbenzene, 1,4-diethylbenzene, and diphenylmethane), aromatic heterocyclic compounds each having an alkyl group or substituted alkyl group having two or more carbon atoms (e.g., 2-ethylfuran, 3-propylthiophene, 4-ethylpyridine, and 4-butylquinoline), and compounds each having a non-aromatic ring condensed to an aromatic ring, which non-aromatic ring has a methylene group at the adjacent position to the aromatic ring (e.g., dihydronaphthalene, indene, indan, tetralin, fluorene, acenaphthene, phenalene, indanone, and xanthene).

The non-aromatic compounds (A4-2) each having a methyl group or methylene group at the adjacent position to an unsaturated bond include, for example, (A4-2a) chain unsaturated hydrocarbons each having a methyl group or methylene group at an "allyl position", and (A4-2b) compounds each having a methyl group or methylene group at the adjacent position to a carbonyl group.

The chain unsaturated hydrocarbons (A4-2a) include, but are not limited to, propylene, 1-butene, 2-butene, 1-pentene, 1-hexene, 2-hexene, 1,5-hexadiene, 1-octene, 3-octene, undecatrines, and other chain unsaturated hydrocarbons each having from about 3 to about 20 carbon atoms. The compounds (A4-2b) include, but are not limited to, ketones (e.g., acetone, methyl ethyl ketone, 3-pentanone, acetophenone, and other chain ketones; and cyclohexanone and other cyclic ketones), carboxylic acids or derivatives thereof (e.g., acetic acid, propionic acid, butanoic acid, pentanoic acid, hexanoic acid, heptanoic acid, phenylacetic acid, malonic acid, succinic acid, glutaric acid, and esters of these acids).

The non-aromatic cyclic hydrocarbons (A5) include (A5-1) cycloalkanes and (A5-2) cycloalkenes.

The cycloalkanes (A5-1) include, but are not limited to, compounds each having a 3- to 30-membered cycloalkane ring, such as cyclopropane, cyclobutane, cyclopentane, cyclohexane, cycloheptane, cyclooctane, cyclononane, cyclodecane, cyclododecane, cyclotetradecane, cyclohexadecane, cyclotetracosane, cyclotriacontane, and derivatives of these compounds. Preferred cycloalkane rings include 5- to 30-membered cycloalkane rings, of which 5- to 20-membered cycloalkane rings are typically preferred.

The cycloalkenes (A5-2) include, but are not limited to, compounds each having a 3- to 30-membered cycloalkene ring, such as cyclopropene, cyclobutene, cyclopentene, cyclooctene, cyclohexene, 1-methyl-cyclohexene, isophorone, cycloheptene, cyclododecene, as well as cyclopentadiene, 1,3-cyclohexadiene, 1,5-cyclooctadiene, and other cycloalkadienes, cyclooctatriene and other cycloalkatrienes, and derivatives of these compounds. Preferred cyclalkenes include compounds each having a 3- to 20-membered ring, of which compounds each having a 3- to 12-membered ring are typically preferred.

The conjugated compounds (A6) include, for example, (A6-1) conjugated dienes, (A6-2) α,β-unsaturated nitriles, and (A6-3) α,β-unsaturated carboxylic acids or derivatives (e.g., esters, amides and acid anhydrides) thereof.

The conjugated dienes (A6-1) include, but are not limited to, butadiene, isoprene, 2-chlorobutadiene, and 2-ethylbutadiene. The conjugated dienes (A6-1) also include, herein, vinyl acetylene and other compounds in which a double bond and a triple bond are conjugated.

The α,β-unsaturated nitriles (A6-2) include, for example, (meth)acrylonitrile. The α,β-unsaturated carboxylic acids or derivatives thereof (A6-3) include, but are not limited to, (meth)acrylic acid; methyl(meth)acrylate, ethyl(meth)acrylate, isopropyl(meth)acrylate, butyl(meth)acrylate, 2-hydroxyethyl(meth)acrylate, and other (meth)acrylic esters; (meth)acrylamide, N-methylol(meth)acrylamide and other (meth)acrylamide derivatives.

The amines (A7) include, but are not limited to, primary or secondary amines such as methylamine, ethylamine, propylamine, butylamine, dimethylamine, diethylamine, dibutylamine, ethylenediamine, 1,4-butanediamine, hydroxylamine, ethanolamine, and other aliphatic amines; cyclopentylamine, cyclohexylamine, and other alicyclic amines; benzylamine, toluidine, and other aromatic amines; pyrrolidine, piperidine, piperazine, indoline, and other cyclic amines to which an aromatic or non-aromatic ring may be condensed.

The aromatic hydrocarbons (A8) include, but are not limited to, benzene, naphthalene, acenaphthylene, phenanthrene, anthracene, naphthacene, aceanthrylene, triphenylene, pyrene, chrysene, naphthacene, picene, perylene, pentacene, coronene, pyranthrene, ovalene, and other aromatic compounds each having at least one benzene ring. Of these aromatic hydrocarbons, preferred are condensed polycyclic aromatic compounds in which at least a plurality of benzene rings (e.g., two to ten benzene rings) are condensed. These aromatic hydrocarbons may each have at least one substituent. Examples of such aromatic hydrocarbons each having a substituent are 2-chloronaphthalene, 2-methoxynaphthalene, 1-methylnaphthalene, 2-methylnaphthalene, 2-methylanthracene, 2-t-butylanthracene, 2-carboxyanthracene, 2-ethoxycarbonylanthracene, 2-cyanoanthracene, 2-nitroanthracene, and 2-methylpentalene. To each of the benzene rings, a non-aromatic carbon ring, an aromatic heterocyclic ring, or a non-aromatic heterocyclic ring may be condensed.

The straight-chain alkanes (A9) include, but are not limited to, methane, ethane, propane, butane, pentane, hexane, heptane, octane, nonane, decane, dodecane, tetradecane, hexadecane, and other straight-chain alkanes each having from about 1 to about 30 carbon atoms and preferably from about 1 to about 20 carbon atoms.

The olefins (A10) may be any of α-olefins and internal olefins each of which may have a substituent (e.g., the aforementioned substituents such as hydroxyl group and acyloxy groups) and also include dienes and other olefins each having plural carbon-carbon double bonds. Examples of the olefins (A10) include ethylene, propylene, 1-butene, 2-butene, isobutene, 1-pentene, 2-pentene, 2,4,4-trimethyl-2-pentene, 1-hexene, 2-hexene, 2,3-dimethyl-2-butene, 3-hexene, 3-hexen-1-ol, 2-hexen-1-ol, 1-octen-3-ol, 1-heptene, 1-octene, 2-octene, 3-octene, 4-octene, 1-nonene, 2-nonene, 1-decene, 1-undecene, 1-dodecene, 1-hexadecene, 1-octadecene, 1,5-hexadiene, 1,6-heptadiene, 1,7-octadiene, 1-acetoxy-3,7-dimethyl-2,6-octadiene, styrene, vinyltoluene, α-methylstyrene, 3-vinylpyridine, 3-vinylthiophene, and other chain olefins; cyclopropene, cyclobutene, cyclopentene, cyclohexene, cycloheptene, cyclooctene, cyclononene, cyclodecene, cycloundecene, cyclododecene, 1,4-cyclohexadiene, 1,4-cycloheptadiene, cyclodecadienes, cyclododecadienes, limonene, 1-p-menthene, 3-p-menthene, carveol, bicyclo[2.2.1]hept-2-ene, bicyclo[3.2.1]oct-2-ene, α-pinene, 2-bornene, and other cyclic olefins.

Each of these compounds capable of forming a radical can be used alone or in combination, and in the latter case, the compounds used in combination may belong to the same or different categories. For example, when two or more types of these compounds, especially two or more types of these compounds belonging to different categories, are used in a reaction with oxygen or another oxygen-atom-containing gas, one of the substrates acts as a co-reacting agent (e.g., co-oxidizing agent) with respect to the other and thereby yields significantly increased reaction rate in some cases.

[Radical Scavenging Compounds (B)]

The radical scavenging compounds (B) may be any compounds as long as they can form a stable compound as a result of the reaction with a radical. Examples of such compounds include (B1) unsaturated compounds, (B2) compounds each having a methine carbon atom, (B3) heteroatom-containing compounds, and (B4) oxygen-atom-containing reactants (e.g., oxygen-atom-containing gases). Each of these compounds may be used alone or in combination.

These compounds may have various substituents within a range not adversely affecting the reaction. Such substituents include, but are not limited to, halogen atoms, hydroxyl group, mercapto group, oxo group, substituted oxy groups (e.g., alkoxy groups, aryloxy groups, and acyloxy groups), substituted thio groups, carboxyl group, substituted oxycarbonyl groups, substituted or unsubstituted carbamoyl groups, cyano group, nitro group, substituted or unsubstituted amino groups, sulfo group, alkyl groups, alkenyl group, alkynyl groups, alicyclic hydrocarbon groups, aromatic hydrocarbon groups, and heterocyclic groups.

The unsaturated compounds (B1) include a wide variety of compounds each having an unsaturated bond. Such compounds include, for example, (B1-1) unsaturated compounds each having an electron attractive group at the adjacent position to a carbon-carbon unsaturated bond [active olefins (electron-deficient olefins) and other active unsaturated compounds], (B1-2) compounds each having a carbon-carbon triple bond, (B1-3) compounds each having an aromatic ring, (B1-4) ketenes, (B1-5) isocyanate or thioisocyanate compounds, and (B1-6) inert olefins.

The active unsaturated compounds (B1-1) include, but are not limited to, methyl(meth)acrylate, ethyl(meth)acrylate, isopropyl(meth)acrylate, phenyl(meth)acrylate, methyl crotonate, ethyl crotonate, methyl 3-methyl-2-butenoate, ethyl 3-methyl-2-butenoate, methyl 2-pentenoate, ethyl 2-pentenoate, methyl 2-octenoate, ethyl 2-octenoate, methyl cinnamate, ethyl cinnamate, methyl 4,4,4-trifluoro-2-butenoate, ethyl 4,4,4-trifluoro-2-butenoate, dimethyl maleate, diethyl maleate, dimethyl fumarate, diethyl fumarate, methyl 3-cyanoacrylate, ethyl 3-cyanoacrylate, and other $\alpha,\beta$-unsaturated esters; vinyl methyl ketone, vinyl ethyl ketone, methyl 1-propenyl ketone, and other $\alpha,\beta$-unsaturated ketones; propenal, crotonaldehyde, and other $\alpha,\beta$-unsaturated aldehydes; acrylonitrile, methacrylonitrile, and other $\alpha,\beta$-unsaturated nitriles; (meth)acrylic acid, crotonic acid, and other $\alpha,\beta$-unsaturated carboxylic acids; (meth)acrylamide, and other $\alpha,\beta$-unsaturated carboxylic acid amides; N-(2-propenylidene) methylamine, N-(2-butenylidene)methylamine, and other $\alpha,\beta$-unsaturated imines; styrene, vinyltoluene, $\alpha$-methylstyrene, $\beta$-methylstyrene, and other styrene derivatives, and other compounds each having an aryl group bonded at the adjacent position to a carbon-carbon unsaturated bond; butadiene, isoprene, 2-chlorobutadiene, 2-ethylbutadiene, vinylacetylene, cyclopentadiene derivatives, and other conjugated dienes (including compounds in which a double bond and a triple bond are conjugated).

The compounds (B1-2) each having a carbon-carbon triple bond include, for example, methylacetylene and 1-butyne. The compounds (B1-3) each having an aromatic ring include, for example, compounds each having a benzene ring, a naphthalene ring, or another aromatic carbon ring; and compounds each having a pyrrole ring, a furan ring, a thiophene ring, or another aromatic heterocyclic ring. The ketenes (B1-4) include, for example, ketene and 2-methylketene. The isocyanate or thioisocyanate compounds (B1-5) include, but are not limited to, methyl isocyanate, ethyl isocyanate, phenyl isocyanate, methyl thioisocyanate, ethyl thioisocyanate and phenyl thioisocyanate.

The inert olefins (B1-6) may be whichever of $\alpha$-olefins and internal olefins and also include dienes and other olefins each having plural carbon-carbon double bonds. Examples of the inert olefins (B1-6) include ethylene, propylene, 1-butene, 2-butene, isobutene, 1-pentene, 2-pentene, 1-hexene, 2-hexene, 3-hexene, 1-heptene, 1-octene, 2-octene, 3-octene, 4-octene, 1-nonene, 1-decene, 1-dodecene, 1,5-hexadiene, 1,6-heptadiene, 1,7-octadiene, and other chain olefins (alkenes); cyclopentene, cyclohexene, cyclooctene, cyclodecene, cyclododecene, and other cyclic olefins (cycloalkenes).

The compounds (B2) each having a methine carbon atom include, for example, the compounds exemplified as the compounds (A3). The one and same compound can be used as the compound (A3) and the compound (B2) in the reaction.

The heteroatom-containing compounds (B3) include, for example, (B3-1) compounds each having a sulfur atom, (B3-2) compounds each having a nitrogen atom, (B3-3) compounds each having a phosphorus atom, and (B3-4) compounds each having an oxygen atom. The compounds (B3-1) each having a sulfur atom include, for example, sulfides and thiols. The compounds (B3-2) each having a nitrogen atom include, for example, amines. The compounds (B3-3) each having a phosphorus atom include, for example, phosphites. The compounds (B3-4) each having an oxygen atom include, for example, N-oxides.

The oxygen-atom-containing reactants (reacting agents) (B4) include, for example, oxygen-atom-containing gases, nitric acid, nitrous acid or salts thereof (hereinafter referred to as "nitric acids"). The oxygen-atom-containing gases include those each having a boiling point (or sublimation point) of less than or equal to 45° C. Such oxygen-atom-containing gases include, but are not limited to, (B4-1) oxygen, (B4-2) carbon monoxide, (B4-3) nitrogen oxides, and (B4-4) sulfur oxides. Each of these oxygen-atom-containing reactants can be used alone or in combination.

The oxygen (B4-1) may be any of molecular oxygen and active oxygen. The molecular oxygen is not specifically limited and includes pure oxygen, oxygen diluted with an inert gas such as nitrogen, helium, argon or carbon dioxide, and air. Molecular oxygen is often used as the oxygen.

The carbon monoxide (B4-2) may be pure carbon monoxide or carbon monoxide diluted with an inert gas. When carbon monoxide is used in combination with oxygen, a carboxylic acid can be obtained in a high yield as a result of the reaction with the compound (A).

The nitrogen oxides (B4-3) include compounds represented by the formula: $N_xO_y$, wherein x is 1 or 2; and y is an integer of from 1 to 6. In these compounds, y is generally an integer of from 1 to 3 when x is 1; and y is generally an integer of from 1 to 6 when x is 2.

Typical examples of the nitrogen oxides are $N_2O$, $NO$, $N_2O_3$, $NO_2$, $N_2O_4$, $N_2O_5$, $NO_3$, and $N_2O_6$. Each of these nitrogen oxides can be used alone or in combination. The nitrogen oxides may be pure substances or mixtures mainly containing nitrogen oxides. Such mixtures mainly containing nitrogen oxides include, exhausted gases formed in oxidation processes with nitric acid.

Preferred nitrogen oxides include, for example, $NO$, $N_2O_3$, $NO_2$ and $N_2O_5$. In this connection, $N_2O_3$ can easily be obtained upon a reaction of dinitrogen monoxide ($N_2O$) and/or nitrogen monoxide (NO) with oxygen. More specifically, $N_2O_3$ can be prepared by introducing dinitrogen monoxide (or nitrogen monoxide) to react and oxygen into a cooled reactor to yield a blue liquid $N_2O_3$. Accordingly, the reaction according to the present invention can be performed by introducing dinitrogen monoxide ($N_2O$) and/or nitrogen monoxide (NO) and oxygen into a reaction system without the previous formation of $N_2O_3$. The nitrogen oxides can be used in combination with oxygen. For example, by using $NO_2$ in combination with oxygen, the yield of the product (e.g., a nitro compound) can further be improved.

The sulfur oxides (B4-4) include compounds represented by formula: $S_pO_q$, wherein p is 1 or 2; and q is an integer of from 1 to 7. In these compounds, q is generally an integer of from 1 to 4 when p is 1; and q is generally 3 or 7 when p is 2.

Such sulfur oxides include, but are not limited to, SO, $S_2O_3$, $SO_2$, $SO_3$, $S_2O_7$ and $SO_4$. Each of these sulfur oxides can be used alone or in combination. As the sulfur trioxide, fuming sulfuric acid containing sulfur trioxide can be employed.

Preferred sulfur oxides include those mainly containing at least one of sulfur dioxide ($SO_2$) and sulfur trioxide ($SO_3$) The sulfur oxide can be used in combination with oxygen. For example, by using sulfur dioxide ($SO_2$) in combination with oxygen, a corresponding sulfonic acid can be obtained in a high yield as a result of the reaction with the compound (A).

The salts of nitric acid or nitrous acid include, but are not limited to, sodium salts, potassium salts, and other alkali metal salts; magnesium salts, calcium salts, barium salts, and other alkaline earth metal salts; silver salts, aluminium salts, zinc salts, and salts of other metals. Preferred salts include alkali metal salts of nitric acid or nitrous acid.

The nitric acids can be supplied as intact to the reaction system or may be supplied in the form of solutions such as aqueous solutions. Alternatively, these components may be formed in the reaction system and may be subjected to the reaction.

The reaction between the compound (A) capable of forming a radical and the radical scavenging compound (B) is performed in the presence of, or in the absence of, a solvent. Such solvents include, but are not limited to, acetic acid, propionic acid, and other organic acids; acetonitrile, propionitrile, benzonitrile, and other nitrites; formamide, acetamide, dimethylformamide (DMF), dimethylacetamide, and other amides; hexane, octane, and other aliphatic hydrocarbons; chloroform, dichloromethane, dichloroethane, carbon tetrachloride, chlorobenzene, trifluoromethylbenzene, and other halogenated hydrocarbons; nitrobenzene, nitromethane, nitroethane, and other nitro compounds; ethyl acetate, butyl acetate, and other esters; and mixtures of these solvents. In may cases, acetic acid and other organic acids, acetonitrile, benzonitrile, and other nitrites, trifluoromethylbenzene, and other halogenated hydrocarbons, ethyl acetate and other esters are used as the solvent.

The ratio of the compound (A) capable of forming a radical to the radical scavenging compound (B) can appropriately selected depending on the types (cost, reactivity) of the two compounds or combinations thereof. For example, the compound (A) may be used in excess (e.g., from about 2 to about 50 times by mole) to the compound (B). Alternatively, the compound (B) may be used in excess to the compound (A).

The process of the present invention has a feature in that the reaction smoothly proceeds under mild conditions. A reaction temperature can appropriately be selected depending on the types of the compound (A) and compound (B) or the type of the target product, and is, for example, from about 0° C. to about 300° C., and preferably about 20° C. to 200° C. The reaction can be performed at atmospheric pressure or under a pressure (under a load). When the reaction is performed under a pressure, the pressure is usually from about 0.1 to about 10 MPa (e.g., from about 0.15 to about 8 MPa, and particularly from about 1 to about 8 MPa). A reaction time can appropriately be selected within a range of, for example, from about 10 minutes to about 48 hours depending on the reaction temperature and pressure.

The reaction can be performed in a batch system, semibatch system, continuous system or another conventional system. By adding the imide catalyst to the reaction system in installments, the target compound can be obtained with a higher conversion or selectivity in many cases.

After the completion of the reaction, reaction products can easily be separated and purified by a conventional technique such as filtration, concentration, distillation, extraction, crystallization, recrystallization, column chromatography, and other separation means, or any combination of these separation means.

The process of the present invention yields an addition or substitution reaction product or a derivative thereof depending on the combination of the compound (A) capable of forming a radical and the radical scavenging compound (B). Such addition or substitution reaction products include, for example, carbon-carbon bonded products (e.g., coupling reaction products), oxidation products, carboxylation products, nitration products, and sulfonation products.

For example, when the heteroatom-containing compound (A1) having a carbon-hydrogen bond at the adjacent position to the heteroatom is used as the compound (A), the adjacent position to the heteroatom is combined with an atom (e.g., a carbon atom) constituting an unsaturated bond of the unsaturated compound (B1), to the methine carbon atom of the compound (B2) having a methine carbon atom, or to the heteroatom of the heteroatom-containing compound (B3), and thereby yields an addition or substitution reaction product or a derivative thereof.

When the compound (A2) having a carbon-heteroatom double bond (e.g., the carbonyl-group-containing compound) is employed as the compound (A), a bond between a carbon atom relating to the carbon-heteroatom double bond (e.g., a carbonyl carbon atom) and an atom adjacent to the carbon atom is broken, and an atomic group containing the carbon-heteroatom double bond (e.g., an acyl group) is combined with the aforementioned position of the compound (B1), (B2) or (B3) to yield an addition or substitution reaction product or a derivative thereof.

When the compound (A3) having a methine carbon atom is used as the compound (A) capable of forming a radical, the methine carbon atom is combined with the aforementioned position of the compound (B1), (B2) or (B3) to yield an addition or substitution reaction product or a derivative thereof.

Generally, the use of the unsaturated compound (B1) as the radical scavenging compound (B) yields an addition reaction product, and the use of the compound (B2) having a methine carbon atom as the compound (B) yields a substitution reaction product (e.g., a coupling product).

The reaction between the oxygen-atom-containing reactant (B4) as the radical scavenging compound (B) with the compound (A) capable of forming a radical yields an organic compound having an oxygen-atom-containing group (e.g., hydroxyl group, oxo group, carboxyl group, nitro group, or sulfur acid group) depending on the type of the oxygen-atom-containing reactant.

According to the process of the present invention, a complicated organic compound can be obtained through one step by using two or more types of the compounds (A) capable of forming a radical and/or the radical scavenging compounds (B) to thereby invite sequential addition or substitution reactions. For example, when the unsaturated compound (B1) and oxygen (B4-1) as the radical scavenging compounds (B) are allowed to react with the compound (A), a group derived from the compound (A) is combined with one of the two carbon atoms constituting the unsaturated bond as mentioned above, and a hydroxyl group derived from the oxygen is introduced into the other carbon atom.

A reaction mechanism in the process of the present invention is not clarified in detail, but is supposed as follows. During the reaction, an oxidized active species [e.g., imido-N-oxy radical (>NO●)] is formed as in the case where the N-hydroxy cyclic imide compound is used as the catalyst, the oxidized active species withdraws a hydrogen from the compound (A) and allows the compound (A) to form a radical, for example, at the carbon atom at the adjacent position to the heteroatom in the compound (A1), at the carbon atom relating to the carbon-heteroatom double bond in the compound (A2), at the methine carbon atom in the compound (A3), or at the carbon atom at the adjacent position to the unsaturated bond in the compound (A4); the thus-formed radical reacts with the compound (B) and thereby yields a corresponding addition or substitution reaction product.

The above-formed addition or substitution reaction product may further undergo, for example, dehydration reaction, cyclization reaction, decarboxylation reaction, rearrangement reaction, or isomerization reaction in the reaction system depending on the structure thereof or reaction conditions, and thereby yields a corresponding derivative.

The reaction between the compound (A) capable of forming a radical and the radical scavenging compound (B) should preferably be performed under conditions with minimal polymerization inhibitors (e.g., hydroquinone). For example, the proportion of the polymerization inhibitor in the reaction system should preferably be less than or equal to 1000 ppm, and more preferably less than or equal to 100 ppm. If the proportion of the polymerization inhibitor exceeds 1000 ppm, a reaction rate is liable to decrease, and the imide catalyst and/or the co-catalyst has to be used in large amounts in some cases. In contrast, when the proportion of the polymerization inhibitor in the reaction system is low, the reaction rate increases to increase a yield, and the reaction results have a high reproducibility to stably yield a target compound. The unsaturated compounds (B1) or other compounds for use in commercial, to which a polymerization inhibitor is added, should preferably be subjected to elimination of the polymerization inhibitor by, for example, distillation, prior to the reaction. The same goes for any reaction in which the compound (A) is allowed to react with the compound (B) in the presence of the imide compound.

By using an appropriate combination of the compound (A) capable of forming a radical and the radical scavenging compound (B) in the reaction according to the present invention, various organic compounds as mentioned below can be obtained.

1. Production of 1,3-Dihydroxy Compounds

A first embodiment of such production will be described below. By catalysis of the imide compound, an alcohol represented by following Formula (2):

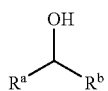

(2)

wherein $R^a$ and $R^b$ are the same or different and are each a hydrogen atom or an organic group, where $R^a$ and $R^b$ may be combined to form a ring with the adjacent carbon atom, is allowed to react with (B4-1) oxygen and (B11) an active olefin represented by following Formula (3):

(3)

wherein $R^c$, $R^d$ and $R^e$ are the same or different and are each a hydrogen atom or an organic group; and Y is an electron attractive group, where $R^c$, $R^d$, $R^e$ and Y may be combined with each other to form a ring with the adjacent carbon atom or carbon-carbon bond, and thereby yields a 1,3-dihydroxy compound represented by following Formula (4):

(4)

wherein $R^a$, $R^b$, $R^c$, $R^d$, $R^e$ and Y have the same meanings as defined above. This reaction can be performed pursuant to a process (a process using a catalytic N-hydroxy cyclic imide compound) described in PCT International Publication No. WO00/35835.

[Alcohols]

The organic group in $R^a$ and $R^b$ in Formula (2) has only to be an organic group that does not adversely affect the reaction (e.g., an organic group that is not reactive under reaction conditions according to the process). Such organic groups include, for example, hydrocarbon groups and heterocyclic groups.

The hydrocarbon groups include aliphatic hydrocarbon groups, alicyclic hydrocarbon groups, and aromatic hydrocarbon groups. Such aliphatic hydrocarbon groups include, but are not limited to, straight- or branched-chain aliphatic hydrocarbon groups (alkyl groups, alkenyl groups, and alkynyl groups) each having from about 1 to about 20 carbon atoms. The alicyclic hydrocarbon groups include, but are not limited to, monocyclic alicyclic hydrocarbon groups (e.g., cycloalkyl groups and cycloalkenyl groups) each having from about 3 to about 20 carbon atoms (preferably having from about 3 to about 15 carbon atoms); and bridged cyclic hydrocarbon groups. The aromatic hydrocarbon groups include, for example, aromatic hydrocarbon groups each having from about 6 to about 14 carbon atoms. These hydrocarbon groups may have various substituents.

Heterocyclic rings constituting the heterocyclic groups in $R^a$ and $R^b$ include aromatic heterocyclic rings and non-aromatic heterocyclic rings. Such heterocyclic rings include heterocyclic rings each containing an oxygen atom as a heteroatom, heterocyclic rings each containing a sulfur atom as a heteroatom, and heterocyclic rings each containing a nitrogen atom as a heteroatom. These heterocyclic groups may have at least one substituent.

The rings formed by $R^a$ and $R^b$ with the adjacent carbon atom include, but are not limited to, cyclopentane, cyclohexane, cyclohexene, cyclododecane, decalin, adamantane, and other non-aromatic carbon rings (cycloalkane rings, cycloalkene rings, and bridged carbon rings) each having from about 3 to about 20 members (preferably from about 3 to about 15 members, more preferably from about 5 to about 15 members, and typically from about 5 to about 8 members). These rings may have at least one substituent (e.g., similar groups to the substituents that the hydrocarbon groups may have). To each of these rings, another ring (a non-aromatic ring or an aromatic ring) may be condensed.

Preferred substituent R includes hydrogen atom, $C_1$-$C_4$alkyl groups, and $C_6$-$C_{14}$ aryl groups. Preferred $R^b$ includes hydrogen atom, $C_1$-$C_{10}$ aliphatic hydrocarbon groups and alicyclic hydrocarbon groups. Alternatively, $R^a$ and $R^b$ are preferably combined to form a non-aromatic carbon ring having from about 3 to about 15 members (particularly from about 5 to about 8 members) with the adjacent carbon atom.

The alcohols represented by Formula (2) include, for example, those exemplified as the primary or secondary alcohols in compounds (A1-1).

Preferred alcohols include secondary alcohols (e.g., 2-propanol, s-butyl alcohol, and other aliphatic secondary alcohols; 1-cyclohexylethanol, and other secondary alcohols each having an aliphatic hydrocarbon group (e.g., a $C_1$-$C_4$ alkyl group, or a $C_6$-$C_{14}$ aryl group) and a non-aromatic carbocyclic group (e.g., a $C_3$-$C_{15}$ cycloalkyl group or a cycloalkenyl group) combined with a carbon atom that is combined with a hydroxyl group; cyclopentanol, cyclohexanol, 2-adamantanol, and other alicyclic secondary alcohols each having from about 3 to about 15 members; 1-phenylethanol, and other aromatic secondary alcohols), and alcohols in which the substituent $R^b$ is a bridged cyclic hydrocarbon group.

[Active Olefins]

The organic groups in $R^c$, $R^d$ and $R^e$ in the active olefins represented by Formula (3) can be any organic groups, as long as they do not adversely affect the reaction (e.g., organic groups that are inert under reaction conditions according to the process of the present invention). Such organic groups include, but are not limited to, halogen atoms, hydrocarbon groups, heterocyclic groups, substituted oxycarbonyl groups (e.g., alkoxycarbonyl groups, aryloxycarbonyl groups, aralkyloxycarbonyl groups, and cycloalkyloxycarbonyl groups), carboxyl group, substituted or unsubstituted carbamoyl groups (N-substituted or unsubstituted amide groups), cyano group, nitro group, sulfur acid radicals (sulfonic acid groups, and sulfinic acid groups), sulfur acid ester groups (sulfonic acid ester groups, and sulfinic acid ester groups), acyl groups, hydroxyl group, alkoxy groups, and N-substituted or unsubstituted amino groups. The carboxyl group, hydroxyl group and amino groups may be protected by a conventional protecting group.

The halogen atoms include fluorine, chlorine, bromine, and iodine atoms. The hydrocarbon groups include, for example, the groups exemplified as the hydrocarbon groups in $R^a$ and $R^b$. These hydrocarbon groups may have at least one substituent. The heterocyclic groups include, for example, the groups exemplified as the heterocyclic groups in $R^a$ and $R^b$. These heterocyclic groups may have at least one substituent. The alkoxycarbonyl groups include, but are not limited to, methoxycarbonyl, ethoxycarbonyl, propoxycarbonyl, isopropoxycarbonyl, butoxycarbonyl, t-butoxycarbonyl, and other $C_1$-$C_6$ alkoxy-carbonyl groups. The aryloxycarbonyl groups include, but are not limited to, phenyloxycarbonyl group. The aralkyloxycarbonyl groups include, for example, benzyloxycarbonyl group. Illustrative cycloalkyloxycarbonyl groups are cyclopentyloxycarbonyl and cyclohexyloxycarbonyl groups.

The substituted carbamoyl groups include, for example, N-methylcarbamoyl, and N,N-dimethylcarbamoyl groups. Illustrative sulfonic acid ester groups are methyl sulfonate, ethyl sulfonate, and other sulfonic acid $C_1$-$C_4$ alkyl ester groups. Illustrative sulfinic acid ester groups are methyl sulfinate, ethyl sulfinate, and other sulfinic acid $C_1$-$C_4$ alkyl ester groups. The acyl groups include, but are not limited to, acetyl, propionyl, and other aliphatic acyl groups (e.g., $C_2$-$C_7$ aliphatic acyl groups), and benzoyl, and other aromatic acyl groups. The alkoxy groups include, but are not limited to, methoxy, ethoxy, propoxy, butoxy, and other alkoxy groups each having from about 1 to about 6 carbon atoms. The N-substituted amino groups include, for example, N,N-dimethylamino, N,N-diethylamino, and piperidino groups.

Preferred $R^c$, $R^d$, and $R^e$ include, for example, hydrogen atom, hydrocarbon groups [e.g., $C_1$-$C_6$ aliphatic hydrocarbon groups (particularly $C_1$-$C_4$ aliphatic hydrocarbon groups), $C_6$-$C_{14}$ aryl groups (e.g., phenyl group), cycloalkyl groups (e.g., cycloalkyl groups each having from about 3 to about 8 members), haloalkyl groups (e.g., trifluoromethyl group, and other $C_1$-$C_6$ haloalkyl group, particularly $C_1$-$C_4$ haloalkyl groups)], heterocyclic groups, substituted oxycarbonyl groups (e.g., $C_1$-$C_6$ alkoxy-carbonyl groups, aryloxycarbonyl groups, aralkyloxycarbonyl groups, and cycloalkyloxycarbonyl groups), carboxyl group, substituted or unsubstituted carbamoyl groups, cyano group, nitro group, sulfur acid groups, sulfur acid ester groups, and acyl groups. Typically preferred $R^c$ and $R^d$ are, for example, hydrogen atom, $C_1$-$C_6$ aliphatic hydrocarbon groups (particularly $C_1$-$C_4$ aliphatic hydrocarbon groups), $C_6$-$C_{14}$ aryl groups (e.g., phenyl group)., cycloalkyl groups (e.g., cycloalkyl groups each having from about 3 to about 8 members), haloalkyl groups (e.g., trifluoromethyl group and other $C_1$-$C_6$ haloalkyl groups, particularly $C_1$-$C_4$ haloalkyl groups)], substituted oxycarbonyl groups (e.g., $C_1$-$C_6$ alkoxy-carbonyl groups, aryloxycarbonyl groups, aralkyloxycarbonyl groups, and cycloalkyloxycarbonyl groups), and cyano group. Typically preferred $R^e$ includes, for example, hydrogen atom, and $C_1$-$C_6$ aliphatic hydrocarbon groups (especially, $C_1$-$C_4$ aliphatic hydrocarbon groups).

The rings formed by $R^c$, $R^d$ and $R^e$ ($R^c$ and $R^d$, $R^c$ and $R^e$, $R^d$ and $R^e$, or $R^c$ and $R^d$ and $R^e$) together with the adjacent carbon atom or carbon-carbon bond include cyclopropane, cyclobutane, cyclopentane, cyclopentene, cyclohexane, cyclohexene, cyclooctane, cyclododecane, and other alicyclic carbon rings (e.g., cycloalkane rings and cycloalkene rings) each having from about 3 to about 20 members. These rings may have at least one substituent, and another ring (a non-aromatic ring or an aromatic ring) may be condensed to each of these rings.

The electron attractive groups Y include, but are not limited to, methoxycarbonyl, ethoxycarbonyl, and other alkoxycarbonyl groups; phenoxycarbonyl, and other aryloxycarbonyl groups; formyl, acetyl, propionyl, benzoyl, and other acyl groups; cyano group; carboxyl group; carbamoyl, N,N-dimethylcarbamoyl, and other substituted or unsubstituted carbamoyl groups; —CH═N—R, where R is, for example, an alkyl group; phenyl, naphthyl, and other aryl groups; vinyl, 1-propenyl, ethynyl, and other 1-alkenyl groups or 1-alkynyl groups.

The rings formed by Y and at least one of $R^c$, $R^d$, and $R^e$ with the adjacent carbon atom or carbon-carbon bond include, but are not limited to, cyclopentadiene ring, pyrrole ring, furan ring, and thiophene ring.

Typical active olefins represented by Formula (3) include the compounds exemplified as the active unsaturated compounds (B1-1).

[Reaction]

The reaction of the alcohol represented by Formula (2) with the active olefin represented by Formula (3) and oxygen can be performed in accordance with the procedure described in the reaction between the compound (A) and the compound (B).

In this reaction, the 1,3-dihydroxy compound represented by Formula (4) is supposed to be formed in the following manner. A 1-hydroxyalkyl radical corresponding to the alcohol represented by Formula (2) is formed in the system, attacks and is added to a carbon atom at the beta-position of the group Y between the two carbon atoms constituting an unsaturated bond of the active olefin represented by Formula (3), and oxygen attacks a radical at the alpha-position formed as a result of the addition and thereby yields the 1,3-dihydroxy compound represented by Formula (4).

In the compound represented by Formula (4) formed as a result of the reaction, when Y is a carboxyl group or an ester group such as alkoxycarbonyl group or aryl oxycarbonyl group, a cyclization reaction may further proceed in the system to yield a furanone derivative (α-hydroxy-γ-butyrolactone derivative) represented by Formula (6), as described later. The yield of the furanone derivative can be improved by controlling the type and proportion of the co-catalyst or further subjecting the product to aging after the addition reaction (or further oxidation reaction). A reaction temperature in the aging period may be set higher than that in the addition reaction. The furanone derivative can also be produced by isolating the compound represented by Formula (4), for example dissolving the isolated compound in a solvent, and heating the solution according to necessity. Such solvents include, but are not limited to, the solvents mentioned later, as well as benzene, toluene, and other aromatic hydrocarbons; cyclohexane and other alicyclic hydrocarbons; acetone, cyclohexanone, and other ketones; diethyl ether, tetrahydrofuran, and other ethers; methanol, ethanol, isopropyl alcohol, and other alcohols. A reaction temperature in this procedure is, for example, from about 0° C. to about 150° C., and preferably from about 30° C. to about 100° C.

2. Production of α-Hydroxy-γ-butyrolactone Derivatives

By catalysis of the imide compound, the alcohol represented by Formula (2) is allowed to react with (B4-1) oxygen and an α,β-unsaturated carboxylic acid derivative represented by following Formula (5):

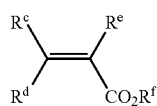

(5)

wherein $R^c$, $R^d$, $R^e$ and $R^f$ are the same or different and are each a hydrogen atom or an organic group, where $R^c$, $R^d$ and $R^e$ may be combined with each other to form a ring with the adjacent carbon atom or carbon-carbon bond, and thereby yields an α-hydroxy-γ-butyrolactone derivative represented by following Formula (6):

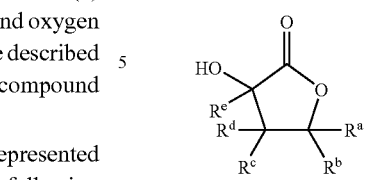

(6)

wherein $R^a$, $R^b$, $R^c$, $R^d$ and $R^e$ have the same meanings as defined above. This reaction can be performed pursuant to the process (a process using a catalytic N-hydroxy cyclic imide compound) described in PCT International Publication No. WO00/35835.

[Alcohols]

The alcohols represented by Formula (2) include similar alcohols to those in the production of the 1,3-dihydroxy compounds.

[α,β-Unsaturated Carboxylic Acid Derivatives]

The substituents $R^c$, $R^d$ and $R^e$ in Formula (5) are similar to $R^c$, $R^d$ and $R^e$ in Formula (3). Organic groups in $R^f$ include organic groups that do not adversely affect the reaction (e.g., organic groups that are inert under reaction conditions according to the process of the present invention) such as hydrocarbon groups and heterocyclic groups. If the compound represented by Formula (5) has a substituted oxycarbonyl group in addition to —$CO_2R^f$ group indicated in Formula (5), the —$CO_2R^f$ group is involved in a cyclization reaction, but the other substituted oxycarbonyl group can remain as intact in the product. The other substituted oxycarbonyl group is therefore included in the inert organic groups.

When at least one of $R^c$ and $R^d$ is an electron attractive organic group, a target α-hydroxy-γ-butyrolactone derivative can be obtained in a significantly high yield. Such electron attractive organic groups include, for example, haloalkyl groups, substituted oxycarbonyl groups, carboxyl group, substituted or unsubstituted carbamoyl groups, cyano group, nitro group, sulfur acid groups, and sulfur acid ester groups.

The substituent $R^f$ is often a hydrogen atom or a hydrocarbon group, and is preferably a $C_1$-$C_6$ alkyl group (especially a $C_1$-$C_4$ alkyl group), a $C_2$-$C_6$ alkenyl group (especially a $C_2$-$C_4$ alkenyl group), or a $C_6$-$C_{10}$ aryl group.

Typical examples of the α,β-unsaturated carboxylic acid derivatives represented by Formula (5) are (meth)acrylic acid; methyl(meth)acrylate, ethyl(meth)acrylate, isopropyl(meth)acrylate, phenyl(meth)acrylate, and other (meth)acrylic esters; crotonic acid; methyl crotonate, ethyl crotonate, and other crotonic esters; 3-methyl-2-butenoic acid; methyl 3-methyl-2-butenoate, ethyl 3-methyl-2-butenoate, and other 3-methyl-2-butenoic esters; 2-pentenoic acid; methyl 2-pentenoate, ethyl 2-pentenoate, and other 2-pentenoic esters; 2-octenoic acid; methyl 2-octenoate, ethyl 2-octenoate, and other 2-octenoic esters; cinnamic acid; methyl cinnamate, ethyl cinnamate, and other cinnamic esters; 4,4,4-trifluoro-2-butenoic acid; methyl 4,4,4-trifluoro-2-butenoate, ethyl 4,4,4-trifluoro-2-butenoate, and other 4,4,4-trifluoro-2-butenoic esters; maleic acid; dimethyl maleate, diethylmaleate, and other maleic esters; fumaric acid; dimethyl fumarate, diethyl fumarate, and other fumaric esters; 3-cyanoacrylic acid; methyl 3-cyanoacrylate, ethyl 3-cyanoacrylate, and other 3-cyanoacrylic esters, and other α,β-unsaturated carboxylic acids each having from about 2 to about 15 carbon atoms or esters thereof (e.g., $C_1$-$C_6$ alkyl esters, $C_2$-$C_6$ alkenyl esters, and aryl esters)

[Reaction]

The reaction of the alcohol represented by Formula (2) with oxygen and the α,β-unsaturated carboxylic acid derivative represented by Formula (5) can be performed pursuant to the process described in the reaction between the compound (A) and the compound (B).

According to the process of the present invention, an α,γ-dihydroxycarboxylic acid derivative (a kind of the compounds represented by Formula (4)) represented by following Formula (7) is formed as a reaction intermediate:

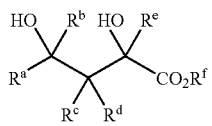
(7)

wherein $R^a$, $R^b$, $R^d$, $R^e$, and $R^f$ have the same meanings as defined above This compound is supposed to be formed in the following manner. A 1-hydroxyalkyl radical corresponding to the alcohol represented by Formula (2) is formed in the system, attacks and is added to the beta-position of the α,β-unsaturated carboxylic acid derivative represented by Formula (5), and oxygen attacks a radical at the alpha-position formed as a result of the addition to yield the compound in question. The formed α,γ-dihydroxycarboxylic acid derivative represented by Formula (7) undergoes cyclization under reaction conditions and thereby yields the target α-hydroxy-γ-butyrolactone derivative represented by Formula (6).

When a primary alcohol is used as the alcohol represented by Formula (2) (i.e., when $R^a$ is a hydrogen atom), a β-acyl-α-hydroxycarboxylic acid derivative of following Formula (8) may be formed in addition to the compound represented by Formula (6). This is provably because an acyl radical [$R^bC(=O)\bullet$] is formed in the system:

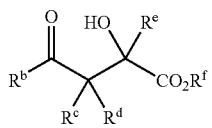
(8)

wherein $R^b$, $R^c$, $R^d$, $R^e$, and $R^f$ have the same meanings as defined above. The α-hydroxy-γ-butyrolactone derivative can also be prepared by isolating the α,γ-dihydroxycarboxylic acid derivative represented by Formula (7), for example, dissolving the same in a solvent, and heating the solution according necessity, as mentioned above.

3. Production of Conjugated Unsaturated Compounds

By catalysis of the imide compound, an alcohol represented by following Formula (2a):

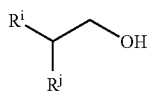
(2a)

wherein $R^i$ and $R^j$ are the same or different and are each a hydrogen atom or an organic group, where $R^i$ and $R^j$ may be combined to form a ring with the adjacent carbon atom, is allowed to react with oxygen and an active olefin represented by following Formula (3a):

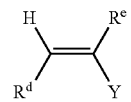
(3a)

wherein $R^d$ and $R^e$ are the same or different and are each a hydrogen atom or an organic group; and Y is an electron attractive group, where $R^d$, $R^e$ and Y may be combined with each other to form a ring with the adjacent carbon atom or carbon-carbon bond, and thereby yields a conjugated unsaturated compound represented by following Formula (9):

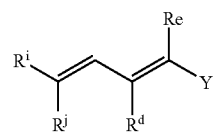
(9)

wherein $R^d$, $R^e$, $R^i$, $R^j$ and Y have the same meanings as defined above. This reaction can be performed pursuant to a process (a process using a catalytic N-hydroxy cyclic imide compound) described in PCT International Publication No. WO00/35835.

Organic groups in $R^i$ and $R^j$ in Formula (2a) are the same as the organic groups in $R^a$ and $R^b$. Rings which are formed by $R^i$ and $R^j$ with the adjacent carbon atom include similar rings to those formed by $R^a$ and $R^b$ with the adjacent carbon atom.

Preferred substituent $R^i$ includes, for example, hydrogen atom, $C_1$-$C_4$ alkyl groups, and $C_6$-$C_{14}$ aryl groups. Preferred $R^j$ includes, for example, hydrogen atom, $C_1$-$C_{10}$ aliphatic hydrocarbon groups (especially $C_1$-$C_{10}$ alkyl groups), and alicyclic hydrocarbon groups (e.g., $C_3$-$C_{15}$ cycloalkyl groups or cycloalkenyl groups; and bridged cyclic hydrocarbon groups). Alternatively, $R^i$ and $R^j$ are preferably combined to form a non-aromatic carbon ring having from about 3 to about 15 members (particularly from about 5 to about 8 members) with the adjacent carbon atom.

The alcohols represented by Formula (2a) include a wide variety of primary alcohols. Typical examples of such alcohols are ethanol, 1-propanol, 1-butanol, 2-methyl-1-propanol, 1-pentanol, 1-hexanol, and other saturated or unsaturated aliphatic primary alcohols each having from about 2 to about 30 (preferably from about 2 to about 20, and more preferably from about 2 to about 15) carbon atoms; cyclopentylmethyl alcohol, cyclohexylmethyl alcohol, and other saturated or unsaturated alicyclic primary alcohols; 2-phenylethyl alcohol, 3-phenylpropyl alcohol, cinnamic alcohol, and other aromatic primary alcohols; and 2-(2-hydroxyethyl)pyridine, and other heterocyclic alcohols.

The compounds represented by Formula (3a) correspond to compounds represented by Formula (3) where $R^c$ is a hydrogen atom. The substituents $R^d$, $R^e$, and Y in Formula (3a) are similar to those in Formula (3).

A reaction can be performed pursuant to the process for producing the 1,3-dihydroxy compound. In this reaction, a compound corresponding to Formula (4) (a compound of Formula (4) where $R^a$=$R^iR^jCH$ group and $R^b$=$R^c$=H) can be formed in addition to the conjugated unsaturated compound represented by Formula (9). When a compound represented by Formula (3a), where Y is a $CO_2R^f$ group, is used as the compound of Formula (3a), a compound corresponding to Formula (6) (a compound of Formula (6) where $R^a$=$R^iR^jCH$ group and $R^b$=$R^c$=H) can be formed in addition to the conjugated unsaturated compound represented by Formula (9).

For example, when n-propyl alcohol is allowed to react with ethyl acrylate, ethyl 2,4-dihydroxyhexanoate corresponding to Formula (4) and 4-ethyl-2-hydroxy-γ-butyrolactone corresponding to Formula (6) are formed under some conditions in addition to the target ethyl sorbate.

The conjugated unsaturated compound represented by Formula (9) is supposed to be formed in the following manner. Initially, a dihydroxy compound corresponding to Formula (4) [a compound of Formula (4) where $R^a$=$R^iR^jCH$ group, and $R^b$=$R^c$=H] is formed, two molecules of water are then eliminated from this compound and thereby yields the compound in question. Reaction products can be separated and purified in the same separation means as above.

4. Production of β-Hydroxyacetal Compounds

By catalysis of the imide compound, an acetal represented by following Formula (10):

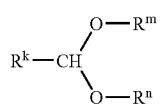

(10)

wherein $R^k$, $R^m$, $R^n$ are the same or different and are each a hydrogen atom or an organic group, where $R^m$ and $R^n$ may be combined to form a ring with the adjacent two oxygen atoms and the carbon atom indicated in the formula, is allowed to react with oxygen and the active olefin represented by Formula (3) and thereby yields a β-hydroxyacetal compound represented by following Formula (11):

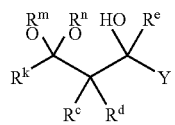

(11)

wherein $R^c$, $R^d$, $R^e$, $R^k$, $R^m$, $R^n$, and Y have the same meanings as defined above. This reaction can be performed pursuant to a process (a process using a catalytic N-hydroxy cyclic imide compound) described in PCT International Publication No. WO00/35835.

In Formula (10), organic groups in $R^k$, $R^m$ and $R^n$ include organic groups similar to those in $R^a$ and $R^b$. Rings formed by $R^m$ and $R^n$ with the adjacent two oxygen atoms and carbon atom include, for example, 1,3-dioxolane ring and 1,3-dioxane ring. To these rings, substituents such as alkyl groups and halogen atoms can be bonded.

Preferred substituent $R^k$ includes, for example, hydrogen atom; $C_1$-$C_{10}$ aliphatic hydrocarbon groups (especially, $C_1$-$C_4$ alkyl groups); alicyclic hydrocarbon groups (cycloalkyl groups, cycloalkenyl groups, and bridged cyclic hydrocarbon groups) each having from about 3 to about 15 carbon atoms; and $C_6$-$C_{14}$ aryl groups. Preferred $R^m$ and $R^n$ include, for example, hydrogen atom; $C_1$-$C_6$ aliphatic hydrocarbon groups (particularly, $C_1$-$C_4$ alkyl groups); and alicyclic hydrocarbon groups each having from about 3 to about 10 carbon atoms. Alternatively, $R^m$ and $R^n$ are preferably combined to form a ring with the adjacent two oxygen atoms and carbon atom.

The acetals represented by Formula (10) include compounds exemplified as the acetals each having a carbon-hydrogen bond at the adjacent position to an oxygen atom in the compounds (A1-3). Typical examples of such acetals include 1,3-dioxolane, 2-methyl-1,3-dioxolane, 2-ethyl-1,3-dioxolane, and other 1,3-dioxolane compounds; 2-methyl-1,3-dioxane, and other 1,3-dioxane compounds; and acetaldehyde dimethyl acetal, and other dialkyl acetals.

The active olefin represented by Formula (3) is the same as stated above. A reaction can be performed according to the process of the present invention for producing an organic compound. Reaction products can be separated and purified in a similar separation means to those mentioned above.

In this reaction, the β-hydroxyacetal compound represented by Formula (11) is supposed to be formed in the following manner. Initially, a 1,1-di-substituted oxyalkyl radial corresponding to the acetal represented by Formula (10) is formed, this radical attacks and is added to a carbon atom at the beta-position of the group Y between the two carbon atoms constituting an unsaturated bond of the active olefin represented by Formula (3), and oxygen attacks a radical at the alpha-position formed as a result of the addition and thereby yields the compound in question.

5. Production of Hydroxy Compounds

By catalysis of the imide compound, a compound having a methine carbon atom and represented by following Formula (12):

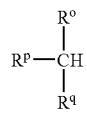

(12)

wherein $R^o$, $R^p$ and $R^q$ are the same or different and are each an organic group, where $R^o$, $R^p$ and $R^q$ may be combined with each other to form a ring with the adjacent carbon atom, is allowed to react with oxygen and the active olefin represented by Formula (3) and thereby yields at least one of hydroxy compounds represented by following Formula (13) and (14):

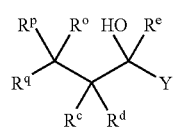

(13)

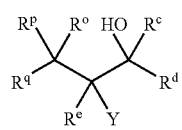

(14)

wherein $R^c$, $R^d$, $R^e$, $R^o$, $R^p$, $R^q$ and Y have the same meanings as defined above. This reaction can be performed pursuant to a process (a process using a catalytic N-hydroxy cyclic imide compound) described in PCT International Publication No. WO00/35835.

The organic groups in $R^o$, $R^p$ and $R^q$ in Formula (12) include organic groups similar to those in $R^a$ and $R^b$. Preferred organic groups include, for example, $C_1$-$C_{10}$ aliphatic hydrocarbon groups (especially, $C_1$-$C_4$ alkyl groups); alicyclic hydrocarbon groups (cycloalkyl groups, cycloalkenyl groups, and bridged cyclic hydrocarbon groups) each having from about 3 to about 15 carbon atoms; and $C_6$-$C_{14}$ aryl groups.

The rings formed by $R^o$, $R^p$ and $R^q$ ($R^o$ and $R^p$, $R^p$ and $R^q$, $R^o$ and $R^q$, or $R^o$ and $R^p$ and $R^q$) together with the adjacent carbon atom include, but are not limited to, cyclopentene, cyclohexane, and other monocyclic alicyclic carbon rings (cycloalkane rings and cycloalkene rings) each having from about 3 to about 20 members (preferably from about 3 to about 15 members, more preferably from about 5 to about 15 members, and typically from about 5 to about 8 members); adamantane ring, perhydroindene ring, decalin ring, perhydrofluorene ring, perhydroanthracene ring, perhydrophenanthrene ring, tricyclo[5.2.1.0$^{2,6}$]decane ring, perhydroacenaphthene ring, perhydrophenalene ring, norbornane ring, norbornene ring, and other bicyclic, tricyclic or tetracyclic bridged carbon rings. These rings may each have at least one substituent.

When $R^o$, $R^p$ and $R^q$ are combined to form a bridged cyclic carbon ring with the adjacent carbon atom, the methine carbon atom indicated in Formula (12) should preferably be a carbon atom at a bridgehead position.

The compounds represented by Formula (12) having a methine carbon atom include, for example, compounds exemplified as the compounds (A3) each having a methine carbon atom, such as the bridged cyclic compounds (A3-1a), the non-aromatic cyclic compounds (A3-1b) each having a hydrocarbon group combined with a ring, and the chain compounds (A3-2) each having a methine carbon atom.

The active olefins represented by Formula (3) are the same as mentioned above. A reaction can be performed according to the process of the present invention for producing an organic compound. Reaction products can be separated and purified in the same separation means as above.

In this reaction, the hydroxy compound represented by Formula (13) or the hydroxy compound represented by Formula (14) is supposed to be formed in the following manner. A radical is formed at the methine carbon position of the compound represented by Formula (12), attacks and is added to a carbon atom at the alpha-position or a carbon atom at the beta-position of the group Y between the two carbon atoms constituting an unsaturated bond of the active olefin represented by Formula (3), and oxygen attacks a radical at the alpha-position or beta-position formed as a result of the addition and thereby yields the hydroxy compound in question.

Of the hydroxy compounds represented by Formula (13) thus prepared, preferred compounds are compounds where $R^o$, $R^p$, and $R^q$ are combined to form a bridged cyclic carbon ring (e.g., adamantane ring) with the adjacent carbon atom, each of $R^c$, $R^d$, and $R^e$ is a hydrogen atom or a $C_1$-$C_4$ alkyl group, Y is an alkoxycarbonyl group (e.g., a $C_1$-$C_4$ alkoxy-carbonyl group), an aryloxycarbonyl group, an acyl group (e.g., a $C_1$-$C_4$ acyl group, or a benzoyl group) or a carboxyl group. Such compounds are useful as, for example, materials for pharmaceuticals, agricultural chemicals, and other fine chemicals, and materials for functional polymers.

6. Production of Carbonyl Compounds (1)

By catalysis of the imide compound, the compound having a methine carbon atom represented by Formula (12) is allowed to react with oxygen and an active olefin represented by following Formula (3b):

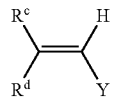

(3b)

wherein $R^c$ and $R^d$ are the same or different and are each a hydrogen atom or an organic group; and Y is an electron attractive group, where $R^c$, $R^d$ and Y may be combined with each other to form a ring with the adjacent carbon atom or carbon-carbon bond, and thereby yields a carbonyl compound represented by following Formula (15):

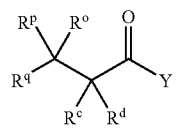

(15)

wherein $R^c$, $R^d$, $R^o$, $R^p$, $R^q$ and Y have the same meanings as defined above. This reaction can be performed pursuant to a process (a process using a catalytic N-hydroxy cyclic imide compound) described in PCT International Publication No. WO00/35835.

This process corresponds to the production of the hydroxy compound in which a compound having a hydrogen atom as $R^e$ is employed as the active olefin represented by Formula (3) In this case, the carbonyl compound represented by Formula (15) is formed instead of, or in addition to, a compound corresponding to Formula (13) ($R^e$=H) and/or a compound corresponding to Formula (14) ($R^e$=H). The proportion of the formed two compounds can be controlled by appropriately selecting reaction conditions such as reaction temperature, amount of the catalyst, and the type of the co-catalyst (metallic compound).

The carbonyl compound represented by Formula (15) is supposed to be formed by the oxidation of the compound corresponding to Formula (13) ($R^e$=H) in a system.

Of the carbonyl compounds represented by Formula (15) thus prepared, preferred compounds are compounds where $R^o$, $R^p$, and $R^q$ are combined to form a bridged cyclic carbon ring (e.g., adamantane ring) with the adjacent carbon atom, each of $R^c$ and $R^d$ is a hydrogen atom or a $C_1$-$C_4$ alkyl group, Y is an alkoxycarbonyl group (e.g., a $C_1$-$C_4$ alkoxy-carbonyl group), an aryloxycarbonyl group, an acyl group (e.g., a $C_1$-$C_4$ acyl group, or a benzoyl group) or a carboxyl group. Such compounds are useful as, for example, materials for pharmaceuticals, agricultural chemicals, and other fine chemicals, and materials for functional polymers.

7. Production of Compounds Having Electron Attractive Group

By catalysis of the imide compound, the compound represented by Formula (12) having a methine carbon atom is allowed to react with oxygen and an active olefin represented by following Formula (3c):

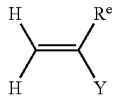
(3c)

wherein $R^e$ is a hydrogen atom or an organic group; and Y is an electron attractive group, and thereby yields a compound having an electron attractive group and represented by following Formula (16):

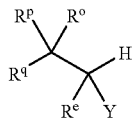
(16)

wherein $R^e$, $R^o$, $R^p$, $R^q$ and Y have the same meanings as defined above. This reaction can be performed pursuant to a process (a process using a catalytic N-hydroxy cyclic imide compound) described in PCT International Publication No. WO00/35835.

This process corresponds to the production of the hydroxy compound where a compound having hydrogen atoms as $R^c$ and $R^d$ is employed as the active olefin represented by Formula (3). In this process, the compound represented by Formula (16) is formed instead of, or in addition to, a compound corresponding to Formula (13) ($R^c=R^d=H$), a compound corresponding to Formula (14) ($R^c=R^d=H$) or a compound corresponding to Formula (15) (only in the case where $R^c=R^d=H$, and $R^e=H$). The proportions of the individual formed compounds can be controlled by appropriately selecting reaction conditions such as reaction temperature, amount of the catalyst, and the type of the co-catalyst (metallic compound).

The compound represented by Formula (16) is supposed to be formed in the following manner. The methylol group of a compound corresponding to Formula (14) ($R^c=R^d=H$) is further oxidized in the system to yield a carboxyl group, and the carboxyl group undergoes decarboxylation to yield the compound in question.

Of the compounds represented by Formula (16) having an electron attractive group thus prepared, preferred compounds include compounds where $R^o$, $R^p$, and $R^q$ are combined to form a bridged cyclic carbon ring (e.g., adamantane ring) with the adjacent carbon atom, $R^e$ is a hydrogen atom or a $C_1$-$C_4$ alkyl group, and Y is an alkoxycarbonyl group (e.g., a $C_1$-$C_4$ alkoxy-carbonyl group), an aryloxycarbonyl group, an acyl group (e.g., a $C_1$-$C_4$ acyl group or a benzoyl group) or a carboxyl group. Such compounds are useful as, for example, materials for pharmaceuticals, agricultural chemicals, and other fine chemicals, and materials for functional polymers.

8. Production of Alcohols

By catalysis of the imide compound and where necessary in the presence of oxygen, the alcohol represented by Formula (2) is allowed to react with the compound represented by Formula (12) having a methine carbon atom and thereby yields an alcohol represented by following Formula (17):

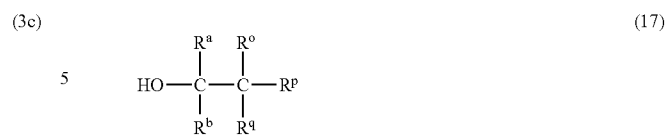
(17)

wherein $R^a$, $R^bR^o$, $R^p$, $R^q$ and Y have the same meanings as defined above. This reaction can be performed pursuant to a process (a process using a catalytic N-hydroxy cyclic imide compound) described in PCT International Publication No. WO00/35835.

The alcohols represented by Formula (2) include similar alcohols as in the production of the 1,3-dihydroxy compounds. The compounds represented by Formula (12) having a methine carbon atom include similar compounds as in the production of the hydroxy compounds. In this process, the compound represented by Formula (12) having a methine carbon atom is supposed to serve as the radical scavenging compound (B2).

A reaction can be performed in accordance with the process of the present invention for producing an organic compound. Reaction products can be separated and purified by the same separation means as above.

In this reaction, the alcohol represented by Formula (17) is supposed to be formed in the following manner. A 1-hydroxyalkyl radical corresponding to the alcohol represented by Formula (2) is formed in a system, attacks the methine carbon atom of the compound represented by Formula (12) and thereby yields the alcohol in question.

9. Production of Coupling Products

By catalysis of the imide compound and where necessary in the presence of oxygen, a compound having a methine carbon atom and represented by following Formula (12a):

(12a)

wherein $R^{o1}$, $R^{p1}$ and $R^{q1}$ are the same or different and are each an organic group, where $R^{o1}$, $R^{p1}$ and $R^{q1}$ may be combined with each other to form a ring with the adjacent carbon atom, is allowed to react with a compound having a methine carbon atom and represented by following Formula (12b):

(12b)

wherein $R^{o2}$, $R^{p2}$ and $R^{q2}$ are the same or different and are each an organic group, where $R^{o2}$, $R^{p2}$ and $R^{q2}$ may be combined with each other to form a ring with the adjacent carbon atom, and thereby yields a coupling product (a hydrocarbon) represented by following Formula (18):

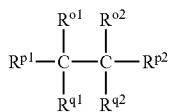
(18)

wherein $R^{o1}$, $R^{p1}$, $R^{q1}$, $R^{o2}$, $R^{p2}$ and $R^{q2}$ have the same meanings as defined above. This reaction can be performed pursuant to a process (a process using a catalytic N-hydroxy cyclic imide compound) described in PCT International Publication No. WO00/35835.

In Formula (12a) and (12b), the organic groups and preferred organic groups in $R^{o1}$, $R^{p1}$, $R^{q1}$, $R^{o2}$, $R^{p2}$, and $R^{q2}$ include organic groups similar to those in $R^o$, $R^p$, and $R^q$. The rings formed by $R^{o1}$, $R^{p1}$, and $R^{q1}$ ($R^{o1}$ and $R^{p1}$, $R^{p1}$ and $R^{q1}$, $R^{q1}$ and $R^{o1}$ol, or $R^{o1}$ and $R^{p1}$ and $R^{q1}$) with the adjacent carbon atom, and the rings formed by $R^{o2}$, $R^{p2}$, and $R^{q2}$ ($R^{o2}$ and $R^{p2}$, $R^{p2}$ and $R^{q2}$, $R^{o2}$ and $R^{q2}$, or $R^{o2}$ and $R^{p2}$ and $R^{q2}$) with the adjacent carbon atom include rings similar to those formed by $R^o$, $R^p$, and $R^q$ with the adjacent carbon atom.

The compounds represented by Formula (12a) and (12b) each having a methine carbon atom include the compounds exemplified as the compounds (A3), such as the bridged cyclic compounds (A3-1a), the non-aromatic cyclic compounds (A3-1b) each having a hydrocarbon group combined with a ring, and the chain compounds (A3-2) each having a methine carbon atom. The compound represented by Formula (12a) and the compound represented by Formula (12b) maybe identical to, or different from, each other.

A reaction can be performed in accordance with the process of the present invention for producing an organic compound. Reaction products can be separated and purified by the same separation means as above.

In this reaction, the coupling product represented by Formula (18) is supposed to be formed in the following manner. A radical is formed at the methine carbon position of the compound represented by Formula (12a), attacks the methine carbon atom of the compound represented by Formula (12b) and thereby yields the coupling product in question.

10. Production of Carbonyl Compounds (2)

By catalysis of the imide compound and where necessary in the presence of oxygen, an aldehyde represented by following Formula (19):

$$R^g CHO \qquad (19)$$

wherein $R^g$ is a hydrogen atom or an organic group, is allowed to react with an olefin represented by following Formula (20):

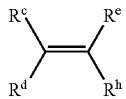
(20)

wherein $R^c$, $R^d$, $R^e$ and $R^h$ are the same or different and are each a hydrogen atom or an organic group, where $R^c$, $R^d$, $R^e$ and $R^h$ may be combined with each other to form a ring with the adjacent carbon atom or carbon-carbon bond, and thereby yields a carbonyl compound represented by following Formula (21):

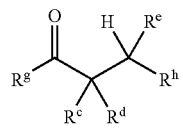
(21)

wherein $R^c$, $R^d$, $R^e$, $R^h$ and $R^g$ have the same meanings as defined above.

In Formula (19), the organic groups in RI include similar organic groups to those in $R^a$ and $R^b$. As the aldehyde represented by Formula (19), the aldehydes exemplified in the carbonyl-group-containing compounds (A2-1) can be used.

In Formula (20), $R^c$, $R^d$ and $R^e$ are the same as above, and the organic groups in $R^h$ include similar organic groups to those in $R^c$, $R^d$ and $R^e$. As the olefin represented by Formula (20), the compounds exemplified as the inert olefins (B1-6) and active unsaturated compounds (B1-1) can be used.

A reaction can be performed in accordance with the process of the present invention for producing an organic compound. Reaction products can be separated and purified by the same separation means as above.

In this reaction, the carbonyl compound represented by Formula (21) is supposed to be formed in the following manner. A corresponding acyl radical is formed from the compound represented by Formula (19), attacks the carbon atom constituting the double bond of the compound represented by Formula (20) and thereby yields the carbonyl compound in question. 11. Production of β-Acyloxycarboxylic Acids or β-Acyloxyketones By catalysis of the imide compound and in the presence of oxygen, the alcohol represented by Formula (2) is allowed to react with an α,β-unsaturated carbonyl compound represented by following Formula (22):

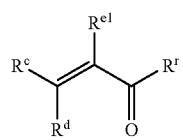
(22)

wherein $R^c$ and $R^d$ are the same or different and are each a hydrogen atom or an organic group; and $R^{e1}$ and $R^r$ are the same or different and are each a hydrogen atom, a hydrocarbon group or a heterocyclic group, where $R^c$ and $R^d$ may be combined to form a ring with the adjacent carbon atom, and thereby yields a β-acyloxycarboxylic acid or β-acyloxyketone represented by following Formula (23):

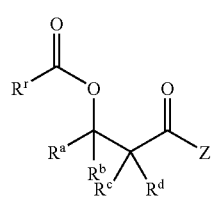
(23)

wherein Z is a hydroxyl group when $R^{e1}$ in Formula (22) is a hydrogen atom, and Z is the substituent $R^{e1}$ when $R^{e1}$ is a hydrocarbon group or a heterocyclic group; and $R^a$, $R^b$, $R^c$, $R^d$, and $R^r$ have the same meanings as defined above. This reaction can be performed pursuant to a process (a process using a catalytic N-hydroxy cyclic imide compound) described in Japanese Patent Application No. 2000-648.

The organic groups, hydrocarbon groups, heterocyclic groups, and the rings formed by $R^c$ and $R^d$ with the adjacent carbon atom include similar groups as mentioned above.

According to this reaction, for example, 2-propanol is allowed to react with methyl vinyl ketone and thereby yields 3-acetoxy-3-methylbutanoic acid. Likewise, 2-propanol is allowed to react with acrolein and thereby yields 3-formyloxy-3-methylbutanoic acid.

The reaction can be performed in accordance with the process of the present invention for producing an organic compound. Reaction products can be separated and purified by the same separation means as above.

In this reaction, the target β-acyloxycarboxylic acid or β-acyloxyketone represented by Formula (23) is supposed to be formed in the following manner. A 1-hydroxyalkyl radical corresponding to the alcohol represented by Formula (2) is formed in the reaction system, attacks and is added to the beta-position of the α,β-unsaturated carbonyl compound represented by Formula (22), oxygen attacks a radical formed at the alpha-position as a result of the addition arid thereby yields an α,β-dihydroxycarbonyl compound represented by following Formula (24):

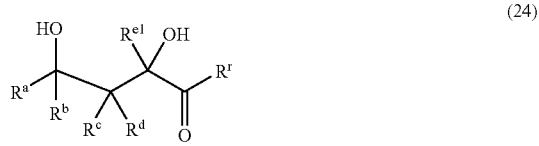

wherein $R^a$, $R^b$, $R^c$, $R^d$, $R^{e1}$ and $R^r$ have the same meanings as defined above. This compound further undergoes rearrangement of an acyl group ($R^rC=O$ group) and oxidation of a carbon atom, to which the acyl group has been bonded, and thereby yields the target β-acyloxycarboxylic acid or β-acyloxyketone represented by Formula (23). When an α,β-unsaturated carbonyl compound represented by Formula (22), where $R^{e1}$ is a hydrogen atom, is used as the starting compound, a corresponding β-acyloxycarboxylic acid is formed. When an α,β-unsaturated carbonyl compound represented by Formula (22), where $R^{e1}$ is a hydrocarbon group or heterocyclic group, is used as the starting compound, a corresponding β-acyloxyketone is formed.

12. Production of Polyacrylamide Polymers

In the presence of the imide compound and the compound (A) capable of forming a radial, an α,β-unsaturated carboxylic acid amide is polymerized under mild conditions and thereby yields a corresponding polyacrylamide polymer [refer to Japanese Patent Application No. 2000-345822 (a process using a catalytic N-hydroxy cyclic imide compound)].

Typical examples of the α,β-unsaturated carboxylic acid amide are (meth)acrylamide, N-methyl(meth)acrylamide, N,N-dimethyl(meth)acrylamide, N-isopropyl(meth)acrylamide, N-phenyl(meth)acrylamide, and crotonamide.

A reaction temperature can appropriately be selected depending on the type of the raw material and other factors and is, for example, from about 0° C. to about 150° C. and preferably from about 10° C. to about 100° C. By controlling the reaction temperature, the molecular weight of the resulting polymer can be controlled. The reaction product can be separated and purified by, for example, precipitation or reprecipitation.

13. Production of Organic Compounds Having Oxygen-Atom-Containing Group

By catalysis of the imide compound, the compound (A) capable of forming a radical is allowed to react with the oxygen-atom-containing reactant (B4) and thereby yields an organic compound having an oxygen-atom-containing group.

This reaction is performed in the presence of, or in the absence of, a solvent. Such solvents include the aforementioned solvents. The amount of the catalytic imide compound is, for example, from about 0.0000001 to about 1 mole, preferably from about 0.000001 to about 0.5 mole, more preferably from about 0.00001 to about 0.4 mole, and often from about 0.0001 to about 0.3 mole, relative to 1 mole of the compound (A). This reaction is significantly accelerated in many cases when a promoter such as the metallic compound (e.g., vanadium compound, molybdenum compound, manganese compound or cobalt compound) is used in combination.

When the oxygen-atom-containing reactant (B4) is in the form of a gas, it may be diluted with an inert gas such as nitrogen gas or argon gas. Each of the oxygen-atom-containing reactants (B4) can be used alone or in combination. By using two or more types of the oxygen-atom-containing reactants (B4) in combination, two or more types of different functional groups can be introduced into the molecule. Such functional groups include, for example, hydroxyl group, oxo group, carboxyl group, nitro group and sulfonic acid group. In the combination use, two types or more of thee oxygen-atom-containing reactants (B4) can be used concurrently or sequentially.

The amount of the oxygen-atom-containing reactant (B4) depends on the type thereof and can appropriately be selected in view of reactivity and operability. For example, when oxygen (B4-1) is used as the oxygen-atom-containing reactant (B4), the amount of oxygen is equal to or more than about 0.5 mole (e.g., equal to or more than about 1 mole), preferably from about 1 to about 100 moles, and more preferably from about 2 to about 50 moles, relative to 1 mole of the compound (A). Oxygen is often used in excess to the compound (A).

When carbon monoxide (B4-2) and oxygen (B4-1) are used in combination as the oxygen-atom-containing reactants (B4), carbon monoxide in an amount of equal to or more than about 1 mole (e.g., from about 1 to about 100 moles) and oxygen in an amount of equal to or more than about 0.5 mole (e.g., from about 0.5 to about 50 moles) are often used relative to 1 mole of the compound (A). In this case, the molar ratio of carbon monoxide to oxygen is from about 1/99 to about 99.99/0.01, and preferably from about 10/90 to about 99/1.

When the nitrogen oxide (B4-3) is used as the oxygen-atom-containing reactant (B4), the amount of the nitrogen oxide can appropriately be selected depending on the types of the nitrogen oxide and the compound (A) and may be equal to or more than 1 mole or may be less than 1 mole, relative to 1 mole of the compound (A). When the amount of the nitrogen oxide (e.g., nitrogen dioxide) is less than 1 mole (e.g., equal to or more than about 0.0001 mole and less than 1 mole), preferably from about 0.001 to about 0.8 mole, and more preferably from about 0.005 to about 0.25 mole, relative to 1 mole of the compound (A), the conversion from the nitrogen oxide and the selectivity of the reaction can significantly be improved.

By using nitrogen dioxide ($NO_2$) in combination with oxygen, the rate of a reaction such as nitration reaction can be significantly improved. In this case, the amount of oxygen is equal to or more than about 0.5 mole (e.g., equal to or more than about 1 mole), preferably from about 1 to about 100 moles, and more preferably from about 2 to about 50 moles, relative to 1 mole of nitrogen dioxide.

When the sulfur oxide (B4-4) is used as the oxygen-atom-containing reactant, the amount of the sulfur oxide can appropriately be selected depending on the types of the sulfur oxide and the compound (A) and is generally from about 1 to about 50 moles, and preferably from about 1.5 to about 30 moles, relative to 1 mole of the compound (A). The reaction can be performed in large excess of the sulfur oxide. When the sulfur oxide (e.g., sulfur dioxide) is used in combination with oxygen, the molar ratio of the sulfur oxide to the oxygen is, for example, from about 10/90 to about 90/10 and more preferably from about 30/70 to about 70/30.

A reaction temperature can appropriately be selected depending on, for example, the types of the compound (A) and the oxygen-atom-containing reactant. For example, when oxygen (B4-1) is used as the oxygen-atom-containing reactant, the reaction temperature is from about 0° C. to about 300° C. and preferably from about 20° C. to about 250° C.

When carbon monoxide (B4-2) and oxygen (B4-1) are used as the oxygen-atom-containing reactants, the reaction temperature is, for example, from about 0° C. to about 200° C. and preferably from about 10° C. to about 150° C. When the nitrogen oxide (B4-3) or sulfur oxide (B4-4) is used as the oxygen-atom-containing reactant (including the case where oxygen is used in combination), the reaction temperature is, for example, from about 0° C. to about 150° C. and preferably from about 10° C. to about 125° C. The reaction can be performed at atmospheric pressure or under a pressure (under a load). When the reaction is performed under a pressure, the pressure is generally from about 0.1 to about 10 MPa, and preferably from about 0.2 to about 7 MPa. The reaction can be performed in a conventional system such as a batch system, semi-batch system or continuous system.

After the completion of the reaction, reaction products can be easily separated and purified by a conventional technique such as filtration, concentration, distillation, extraction, crystallization, recrystallization, adsorption, column chromatography and other separation means, or any combination of these separation means.

This process can produce a reaction product corresponding to the oxygen-atom-containing reactant in a high yield under mild conditions.

Specifically, when oxygen (B4-1) is used as the oxygen-atom-containing reactant, an oxidation reaction proceeds and thereby yields a corresponding oxidation product [refer to Japanese Unexamined Patent Application Publications No. 8-38909, No. 9-327626, No. 10-286467, and No. 2000-219650 (processes using catalytic N-hydroxy cyclic imide compounds)]. For example, when the heteroatom-containing compound (A1) having a carbon-hydrogen bond at the adjacent position to the heteroatom is used as the compound (A), a carbon atom at the adjacent position to the heteroatom is oxidized. For example, a primary alcohol yields a corresponding aldehyde or carboxylic acid, and a secondary alcohol yields a corresponding ketone. A 1,3-diol yields a corresponding hydroxyketone, and a 1,2-diol yields a corresponding a carboxylic acid as a result of oxidative cleavage [refer to Japanese Unexamined Patent Application Publications No. 2000-212116 and NO. 2000-219652 (processes using catalytic N-hydroxy cyclic imide compounds)]. An ether yields a corresponding ester or acid anhydride [refer to Japanese Unexamined Patent Application Publication No. 10-316610 (a process using a catalytic N-hydroxy cyclic imide compound)]. In addition, a primary or secondary alcohol yields hydrogen peroxide [refer to PCT International Publication No. $WO_{00/46145}$ (a process using a catalytic N-hydroxy cyclic imide compound)].

When the compound (A2) having a carbon-heteroatom double bond is used as the compound (A), an oxidation product corresponding to the type of the heteroatom can be obtained. For example, by oxidizing a ketone, a carboxylic acid or another product is produced as a result of cleavage. For example, a cyclic ketone such as cyclohexanone yields a dicarboxylic acid such as adipic acid. By using the heteroatom-containing compound (A1) having a carbon-hydrogen bond at the adjacent position to the heteroatom, such as a secondary alcohol (e.g., benzhydrol), is used as a co-reactant (co-oxidizing agent), a Baeyer-Villiger type reaction proceeds under mild conditions. As a result, a cyclic ketone yields a corresponding lactone, and a chain ketone yields a corresponding ester in high yields [refer to PCT International Publication No. WO99/50204 (cases where catalytic N-hydroxy cyclic imide compounds are used)]. In addition, an aldehyde yields a corresponding carboxylic acid.

By using the compound (A3) having a methine carbon atom as the compound (A), an alcohol derivative having a hydroxyl group introduced into the methine carbon in a high yield. For example, by oxidizing a bridged cyclic hydrocarbon (A3-1a) such as adamantane, alcohol derivatives each having a hydroxyl group at a bridgehead position, such as 1-adamantanol, 1,3-adamantanediol and 1,3,5-adamantanetriol, can be produced with high selectivity. The chain compound (A3-2) having a methine carbon atom, such as isobutane, can yield a tertiary alcohol such as t-butanol in a high yield [refer to Japanese Unexamined Patent Application Publication No. 10-310543 (a process using a catalytic N-hydroxy cyclic imide compound)].

By using the compound (A4) having a carbon-hydrogen bond at the adjacent position to an unsaturated bond as the compound (A), the adjacent position to the unsaturated bond is efficiently oxidized and thereby yields, for example, an alcohol, carboxylic acid or ketone. For example, a compound having a methyl group at the adjacent position to an unsaturated bond yields a primary alcohol or carboxylic acid in a high yield [refer to Japanese Unexamined Patent Application Publications No. 8-38909, No. 9-327626 and No. 11-106377 (processes using catalytic N-hydroxy cyclic imide compounds)]. Likewise, a compound having a methylene group or methine group at the adjacent position to an unsaturated bond yields a secondary or tertiary alcohol, ketone or carboxylic acid, depending on reaction conditions.

More specifically, an aromatic compound having an alkyl group or a lower-order oxidized group thereof combined with an aromatic ring yields an aromatic carboxylic acid having a carboxyl group combined with the aromatic ring as a result of oxidation of the alkyl group or the lower-order oxidized group thereof. Such lower-order oxidized groups include, for example, hydroxy alkyl groups, formyl group, formylalkyl groups, and alkyl groups each having an oxo group. For example, benzoic acid is obtained from toluene, ethylbenzene, isopropylbenzene, benzaldehyde, or mixtures thereof; terephthalic acid is obtained from p-xylene, p-isopropyltoluene, p-diisopropylbenzene, p-tolualdehyde, p-toluic acid, p-carboxybenzaldehyde, or mixtures thereof; isophthalic acid is obtained from m-xylene, m-tolualdehyde, m-carboxybenzaldehyde, or mixtures thereof; trimellitic acid is obtained from pseudocumene, dimethylbenzaldehyde, dimethylbenzoic acid, or mixtures thereof; pyromellitic acid is obtained from durene, trimethylbenzaldehyde, trimethylbenzoic acid, or mixtures thereof; 3-quinolinecarboxylic acid is obtained from, for example, 3-methylquinoline, respectively in high yields. In addition, nicotinic acid is obtained from β-picoline.

For example, a compound having a methylene group at the adjacent position to a carbon-carbon double bond yields a secondary alcohol or ketone. In this case, by using a cobalt(II) salt of an acid having a pKa of less than or equal to 8.0, such as cobalt(II) acetate or cobalt(II) nitrate, is used as the promoter, a corresponding conjugated unsaturated carbonyl compound having an oxo group introduced into the carbon atom of the methylene group can be obtained in a high yield. More specifically, valencene yields nootkatone in a high yield.

By using the non-aromatic cyclic hydrocarbon (A5) as the compound (A), an alcohol, hydroperoxide or ketone having a hydroxyl group, hydroperoxy group or oxo group introduced into a carbon atom constituting a ring is obtained. Under some reaction conditions, the ring is oxidatively cleaved and yields a corresponding dicarboxylic acid. For example, by appropriately selecting the conditions, cyclohexane can yield cyclohexyl alcohol, cyclohexyl hydroperoxide, cyclohexanone or adipic acid with high selectivity. Likewise, a cycloalkane such as cyclohexane yields a bis(1-hydroxycycloalkyl)peroxide such as bis(1-hydroxycyclohexyl)peroxide [refer to Japanese Patent Application No. 2000-345824 (a process using a catalytic N-hydroxy cyclic imide compound)]. By using a strong acid as the promoter, adamantane can yield adamantanone in a high yield [refer to Japanese Unexamined Patent Application Publication No. 10-309469 (a process using a catalytic N-hydroxy cyclic imide compound)].

When the conjugated compound (A6) is used as the compound (A), a variety of compounds is formed depending on the structure of the conjugated compound. For example, a conjugated diene yields an alkenediol or other products as a result of oxidation. Specifically, butadiene yields, for example, 2-butene-1,4-diol and/or 1-butene-3,4-diol as a result of oxidation. When an α,β-unsaturated nitrile or α,β-unsaturated carboxylic acid or a derivative thereof is oxidized, the α,β-unsaturated bonding position is selectively oxidized and is converted into a single bond, and the beta-position is converted into a formyl group, an acetal group (when the reaction is performed in the presence of an alcohol) or an acyloxy group (when the reaction is performed in the presence of a carboxylic acid) in the resulting compound. More specifically, by oxidizing acrylonitrile and methyl acrylate in the presence of methanol, 3,3-dimethoxypropionitrile and methyl 3,3-dimethoxypropionate are respectively formed.

When the amine (A7) is used as the compound (A), a corresponding Schiff base or oxime is formed. When the aromatic compound (A8) is used as the compound (A) in the co-existence of, for example, the compound (A4) having a carbon-hydrogen bond at the adjacent position to an unsaturated bond (e.g., fluorene) as the co-reactant (co-oxidizing agent), a corresponding quinone is formed in a good yield [refer to Japanese Unexamined Patent Application Publications No. 11-226416 and No. 11-228484 (processes using catalytic N-hydroxy cyclic imide compounds)]. The straight-chain alkane (A9) yields, for example, an alcohol, ketone or carboxylic acid.

By using the olefin (A10) as the compound (A), a corresponding epoxy compound can be obtained [refer to Japanese Unexamined Patent Application Publication No. 11-49764 and PCT International Publication No. WO99/50204 (processes using catalytic N-hydroxy cyclic imide compounds)]. Specifically, when the heteroatom-containing compound (A1) having a carbon-hydrogen bond at the adjacent position to the heteroatom, such as a secondary alcohol, or the compound (A4) having a carbon-hydrogen bond at the adjacent position to an unsaturated bond is used as the co-reactant (co-oxidizing agent), an epoxidation reaction proceeds under mild conditions and thereby yields the corresponding epoxide in a good yield.

By allowing at least one compound selected from cycloalkanes, cycloalkanols and cycloalkanones to react with ammonia and oxygen (B4-1) as the oxygen-atom-containing reactant in the presence of the catalytic imide compound, a corresponding lactam is obtained [refer to Japanese Patent Application No. 2000-345823 (a process using a catalytic N-hydroxy cyclic imide compound)]. More specifically, by allowing at least one compound selected from cyclohexane, cyclohexanol and cyclohexanone to react with ammonia and oxygen in the presence of the catalyst, ε-caprolactam is obtained.

By using carbon monoxide (B4-2) and oxygen (B4-1) as the oxygen-atom-containing reactants, a carboxylation reaction smoothly proceeds and thereby yields a corresponding carboxylic acid in a good yield [refer to Japanese Unexamined Patent Application Publication No. 11-239730 (a process using a catalytic N-hydroxy cyclic imide compound)]. For example, when the compound (A3) having a methine carbon atom is used as the compound (A), a carboxyl group is introduced into the methine carbon atom. Likewise, in the compound (A4) having a carbon-hydrogen bond at the adjacent position to an unsaturated bond, a carboxyl group is introduced into a carbon atom relating to the carbon-hydrogen bond. The non-aromatic cyclic hydrocarbon (A5), such as cyclohexane, yields a carboxylic acid having a carboxyl group combined with a carbon atom constituting a ring.

When the nitrogen oxide (B4-3) is used as the oxygen-atom-containing reactant, a nitration reaction predominantly proceeds and thereby yields, for example, a corresponding nitro compound [refer to Japanese Unexamined Patent Application Publication No. 11-239730 (a process using a catalytic N-hydroxy cyclic imide compound)]. For example, when the compound (A3) having a methine carbon atom is used as the compound (A), the methine carbon atom is nitrated. Likewise, when the compound (A4) having a carbon-hydrogen bond at the adjacent position to an unsaturated bond is used, a carbon atom relating to the carbon-hydrogen bond is nitrated. The non-aromatic cyclic hydrocarbon (A5), such as cyclohexane, yields a corresponding cyclic nitro compound having a nitro group combined with a carbon atom constituting a ring. Even the straight-chain alkane (A9), such as hexane, can yield a corresponding nitroalkane. When nitrogen dioxide is used as the oxygen-atom-containing reactant, the nitration reaction can efficiently proceed by using the substrate in excess to nitrogen dioxide [refer to Japanese Unexamined Patent Application Publication No. 11-136339 (a process using a catalytic N-hydroxy cyclic imide compound)].

When a compound having a methyl group at the adjacent position to an aromatic ring (at the "benzyl position"), such as toluene, is used as the compound (A), a nitro group is introduced into the carbon atom of the methyl group. Under some conditions, the methyl group is converted into a formyl group and thereby yields a corresponding aromatic aldehyde (e.g., benzaldehyde), or a nitro group is introduced into the aromatic ring in the resulting compound. The use of a compound having a methylene group at the adjacent position to an aromatic ring (e.g., ethylbenzene) as the substrate yields a nitro compound (e.g., α-nitrobenzene), in which the methylene group is nitrated, and under some reaction conditions, yields an oxime compound (e.g., acetophenone oxime) where the methylene group is converted into an oxime.

By using nitrogen monoxide as the oxygen-atom-containing reactant, an ether can yield a corresponding aldehyde as a result of cleavage of the ether bond [Japanese Unexamined Patent Application Publications No. 11-315036 and No. 11-254977 (processes using catalytic N-hydroxy cyclic imide compounds)]. For example, phthalan can yield phthalaldehyde in a high yield. Likewise, by using nitrogen monoxide as the oxygen-atom-containing reactant, a cycloalkane yields a corresponding cycloalkanone oxime [refer to Japanese Patent Application No. 2000-157356 (a process using a catalytic N-hydroxy cyclic imide compound)]. For example, cyclohexane yields cyclohexanone oxime.

By allowing a chain or cyclic compound having a methylene group to react with the nitrogen oxide such as nitrogen monoxide in the presence of the catalytic imide compound and a halogen (e.g., chlorine) or a Beckmann rearrangement catalyst, a corresponding amide or lactam is obtained [refer to Japanese Patent Application No. 11-372177 (a process using a catalytic N-hydroxy cyclic imide compound)]. For example, cyclohexane yields ε-caprolactam.

When the nitric acids are used as the oxygen-atom-containing reactant, a nitration reaction predominantly proceeds and thereby yields, for example, a corresponding nitro compound, as in the use of the nitrogen oxide (B4-3) [refer to Japanese Patent Application No. 2000-58054 (a process using a catalytic N-hydroxy cyclic imide compound)]. For example, when the compound (A4) having a carbon-hydrogen bond at the adjacent position to an unsaturated bond is used as the substrate, a carbon atom relating to the carbon-hydrogen bond is nitrated. When the compound (A3) having a methine carbon atom is used as the substrate, the methine carbon atom is nitrated. When the non-aromatic cyclic hydrocarbon (A5) is used as the substrate, a nitro group is introduced into a carbon atom constituting a ring. In this case, a cycloalkane, such as cyclohexane, yields a corresponding nitrocycloalkane. In the non-aromatic heterocyclic compound having a carbon-hydrogen bond at the adjacent position to the heteroatom, a carbon atom relating to the carbon-hydrogen bond is nitrated. Likewise, the straight-chain alkane (A9), such as hexane, yields a corresponding nitroalkane.

This reaction is supposed to proceed in the following manner. The imide compound reacts with the nitric acids and thereby yields an imido-N-oxy radical, the radical withdraws a hydrogen atom from the substrate and thereby yields another radical, and to the resulting radical, nitrogen dioxide formed in the reaction system is added and thereby yields a corresponding nitro compound.

When the sulfur oxide (B4-4) is used as the oxygen-atom-containing reactant, a sulfonation and/or sulfination reaction proceeds and thereby yields a corresponding organic sulfur acid or a salt thereof. For example, when the compound (A3) having a methine carbon atom is used as the compound (A), a sulfur acid group is introduced into the methine carbon atom. When the compound (A4) having a carbon-hydrogen bond at the adjacent position to an unsaturated bond is used, a sulfur acid group (e.g., a sulfonic acid group or sulfinic acid group) is introduced into a carbon atom relating to the carbon-hydrogen bond. The non-aromatic cyclic hydrocarbon (A5), such as cyclohexane, yields an organic sulfur acid having a sulfur acid group combined with a carbon atom constituting a ring. The formed organic sulfur acid can be converted into a corresponding salt thereof according to conventional techniques. For example, the salt can be obtained by reacting the organic sulfur acid with an alkali metal hydroxide, alkali metal carbonate, alkali metal hydrogencarbonate, alkaline earth metal hydroxide, alkaline earth metal carbonate, amine, thiourea, or isothiourea in an appropriate solvent such as water.

INDUSTRIAL APPLICABILITY

As thus described, the present invention can produce, for example, organic compounds each having an oxygen-atom-containing group such as hydroxyl group, oxo group, carboxyl group, nitro group or sulfonic acid group, products as a result of the formation of a carbon-carbon bond or derivatives thereof (e.g., cyclized derivatives) with high selectivity in high yields as a result of addition or substitution reactions under mild conditions. In addition, the present invention can introduce such an oxygen-atom-containing group into an organic substrate under mild conditions.

The catalyst of the present invention is highly stable and can maintain its catalytic activity for a long time. The catalyst exhibits high catalytic activity even in a small amount in a radical reaction and is highly stable in a reaction at high temperatures.

EXAMPLES

The present invention will be illustrated in further detail with reference to several examples below, which are not intended to limit the scope of the invention. Reaction products were identified by NMR, IR and/or GC-MS.

Example 1

A mixture of 2 mmol of p-xylene, 0.4 mmol of N-acetoxyphthalimide, 0.01 mmol of cobalt(II) acetate, 0.01 mmol of manganese(II) acetate and 5 ml of acetic acid was stirred at 100° C. in an atmosphere of oxygen gas (1 atm=0.1 MPa) for 14 hours and thereby yielded terephthalic acid and p-toluic acid in yields of 92% and 1%, respectively.

Example 2

A mixture of 2 mmol of p-xylene, 0.4 mmol of N-acetoxyphthalimide, 0.01 mmol of cobalt(II) acetate and 5 ml of acetic acid was stirred at 100° C. in an atmosphere of oxygen gas (1 atm=0.1 MPa) for 14 hours and thereby yielded terephthalic acid and p-toluic acid in yields of 91% and 1%, respectively.

Example 3

A mixture of 2 mmol of p-xylene, 0.2 mmol of N-acetoxyphthalimide, 0.01 mmol of cobalt(II) acetate and 2 ml of acetic acid was stirred at 100° C. in an atmosphere of oxygen gas (1 atm=0.1 MPa) for 14 hours and thereby yielded terephthalic acid and p-toluic acid in yields of 89% and 1%, respectively.

Example 4

A mixture of 2 mmol of p-xylene, 0.1 mmol of N-acetoxyphthalimide, 0.01 mmol of cobalt(II) acetate and 3 ml of acetic acid was stirred at 150° C. in an atmosphere of air (30 atm=3 MPa) for 3 hours and thereby yielded terephthalic acid in a yield of 90%. The yield of p-toluic acid was less than 1%.

Example 5

A mixture of 1 mmol of 3-methylquinoline, 0.1 mmol of N-acetoxyphthalimide, 0.02 mmol of cobalt(II) acetate, 0.001 mmol of manganese(II) acetate, 0.1 mmol of nitrogen dioxide, and 5 ml of acetic acid was stirred at 110° C. in an atmosphere of oxygen gas (1 atm=0.1 MPa) for 15 hours and thereby yielded 3-quinolinecarboxylic acid in a yield of 76% with a conversion from 3-methylquinoline of 89%.

The above procedure was repeated, except that N-hydroxyphthalimide was used instead of N-acetoxyphthalimide, and thereby yielded 3-quinolinecarboxylic acid in a yield of 63% with a conversion from 3-methylquinoline of 76%.

Example 6

In a 500-ml titanium autoclave, 15.36 g (0.113 mol) of p-toluic acid, 1.16 g (5.65 mmol) of N-acetoxyphthalimide, 0.112 g (0.45 mmol) of cobalt(II) acetate tetrahydrate, 0.277 g (1.13 mmol) of manganese(II) acetate tetrahydrate and 107 g of acetic acid were placed, the resulting mixture was stirred at 150° C. in an atmosphere of a mixture of oxygen and nitrogen gases (1:1) [4 MPa (gauge pressure)] for 1 hour and thereby yielded terephthalic acid in a yield of 95.6% with a conversion from p-toluic acid of 97.4%. A small amount of 4-carboxybenzaldehyde was by-produced.

Example 7

In a 500-ml titanium autoclave, 15.36 g (0.113 mol) of p-toluic acid, 0.232 g (1.13 mmol) of N-acetoxyphthalimide, 0.112 g (0.45 mmol) of cobalt(II) acetate tetrahydrate, 0.277 g (1.13 mmol) of manganese(II) acetate tetrahydrate and 107 g of acetic acid were placed, the resulting mixture was stirred at 170° C. in an atmosphere of a mixture of oxygen and nitrogen gases (1:1) [4 MPa (gauge pressure)] for 1 hour and thereby yielded terephthalic acid in a yield of 74.4% with a conversion from p-toluic acid of 77.5%. A small amount of 4-carboxybenzaldehyde was by-produced.

Example 8

In a 500-ml titanium autoclave, 15.36 g (0.113 mol) of p-toluic acid, 0.232 g (1.13 mmol) of N-acetoxyphthalimide, 0.79 mmol of cobalt(II) acetate tetrahydrate, 0.79 mmol of manganese(II) acetate tetrahydrate and 107 g of acetic acid were placed, the resulting mixture was stirred at 150° C. in an atmosphere of a mixture of oxygen and nitrogen gases (1:1) [4 MPa (gauge pressure)] for 1 hour and thereby yielded terephthalic acid in a yield of 70.6% with a conversion from p-toluic acid of 74.3%. A small amount of 4-carboxybenzaldehyde was by-produced.

Example 9

In a 350-ml reactor made of 316 stainless steel, 3.50 g (26.1 mmol; concentration in the system: 5% by weight) of durene, 1.07 g (5.22 mmol) of N-acetoxyphthalimide, 0.025 g (0.10 mmol) of cobalt(II) acetate tetrahydrate, 0.065 g (0.26 mmol) of manganese(II) acetate tetrahydrate, and acetic acid were placed, the reactor was tightly sealed, and the inside pressure was increased to 4 MPa (gauge pressure) using a gaseous mixture containing 50% of oxygen gas and 50% of nitrogen gas. The temperature of the resulting mixture was elevated on an oil bath and was held at 150° C. Four hours later, the reaction mixture was cooled to terminate the reaction. As a result, pyromellitic acid was obtained in a yield of 49.4% with a conversion from durene of 100%. In this procedure, methyltricarboxybenzene (yield: 20.5%), dimethylterephthalic acid (yield: 2.2%) and trimethylbenzoic acid (yield: 1.6%) were by-produced.

The above procedure was repeated, except that N-hydroxyphthalimide was used instead of N-acetoxyphthalimide, and yielded pyromellitic acid in a yield of 20.9% with a conversion from durene of 100%. In this procedure, methyltricarboxybenzene (yield: 34.7%), dimethylterephthalic acid (yield: 3.3%) and trimethylbenzoic acid (yield: 1.5%) were by-produced.

Example 10

In a 350-ml reactor made of 316 stainless steel, 0.5 mol (concentration in the system: 5% by weight) of durene, 0.1 mol of N-acetoxyphthalimide, 0.002 mol of cobalt(II) acetate tetrahydrate, 0.005 mol of manganese(II) acetate tetrahydrate, and acetic acid were placed, the reactor was tightly sealed, and the inside pressure was increased to 4 MPa (gauge pressure) using a gaseous mixture containing 50% of oxygen gas and 50% of nitrogen gas. The resulting mixture was stirred at 100° C. for 1 hour and then at 150° C. for 3 hours. As a result, pyromellitic acid was obtained in a yield of 52.5% with a conversion from durene of 100%. In this procedure, methyltricarboxybenzene (yield: 26.1%), dimethylterephthalic acid (yield: 1.1%) and trimethylbenzoic acid (yield: 0.6%) were by-produced.

Example 11

In a 300-ml reactor made of 316 stainless steel, 36 g (427.7 mmol) of cyclohexane, 175.3 mg (0.855 mmol) of N-acetoxyphthalimide, 31.98 mg (0.128 mmol) of cobalt(II) acetate tetrahydrate, 45.72 mg (0.128 mmol) of acetylacetonatocobalt(II), and 44 g of acetic acid were placed, the reactor was tightly sealed, and the inside pressure was increased to 5 MPa (gauge pressure) using a gaseous mixture containing 50% of oxygen gas and 50% of nitrogen gas. The temperature of the reaction mixture was elevated on an oil bath and was held at 125° C. Gas absorption initiated immediately after the temperature of the mixture reached 125° C., and 60 minutes layer, the reaction mixture was cooled to terminate the reaction. To the resulting reaction mixture, 120 g of acetic acid was added to dissolve all the solid matters, and the resulting solution was subjected to analysis. As a result, adipic acid was obtained with a selectivity of 60.4% and a conversion from cyclohexane of 18.2%. In this procedure, glutaric acid (selectivity: 7.7%), succinic acid (selectivity: 2.9%), cyclohexanone (selectivity: 17.5%), cyclohexanol (selectivity: 10.3%) and cyclohexyl acetate (selectivity: 1.2%) were by-produced.

Example 12

In a 300-ml reactor made of 316 stainless steel, 36 g (427.7 mmol) of cyclohexane, 175.3 mg (0.855 mmol) of N-acetoxyphthalimide, 42.64 mg (0.511 mmol) of cobalt(II) acetate tetrahydrate, 60.96 mg (0.511 mmol) of acetylacetonatocobalt(II), and 44 g of acetic acid were placed, the reactor was tightly sealed, and the inside pressure was increased to 5 MPa (gauge pressure) using a gaseous mixture containing 50% of oxygen gas and 50% of nitrogen gas. The temperature of the reaction mixture was elevated on an oil bath and was held at 125° C. Gas absorption initiate immediately after the temperature of the liquid reached 125° C., and 20 minutes layer, the reaction mixture was cooled to terminate the reaction. To the resulting reaction mixture, 120 g of acetic acid was added to dissolve all the solid matters, and the resulting solution was subjected to analysis. As a result, adipic acid was obtained with a selectivity of 61.2% and a conversion from cyclohexane of 23.0%. In this procedure, glutaric acid (selectivity:

9.7%), succinic acid (selectivity: 4.1%), cyclohexanone (selectivity: 15.7%), cyclohexanol (selectivity: 8.6%) and cyclohexyl acetate (selectivity: 0.7%) were by-produced.

Example 13

A mixture of 2 mmol of p-xylene, 0.1 mmol of N-acetoxyphthalimide, 0.01 mmol of cobalt(II) acetate, 0.01 mmol of manganese(II) acetate and 2 ml of acetic acid was stirred at 100° C. in an atmosphere of oxygen gas (1 atm=0.1 MPa) for 14 hours and thereby yielded terephthalic acid, p-toluic acid and p-carboxybenzaldehyde in yields of 79%, 8% and 5%, respectively.

Example 14

A mixture of 2 mmol of p-xylene, 0.05 mmol of N,N'-diacetoxypyromellitic diimide, 0.01 mmol of cobalt(II) acetate, 0.01 mmol of manganese(II) acetate and 2 ml of acetic acid was stirred at 100° C. in an atmosphere of oxygen gas (1 atm=0.1 MPa) for 14 hours and thereby yielded terephthalic acid, p-toluic acid and p-carboxybenzaldehyde in yields of 78%, 14% and 5%, respectively.

Preparation Example 1 (Preparation of N-Benzoyloxyphthalimide)

In a 3-L flask equipped with a stirrer and thermometer, 100 g (613 mmol) of N-hydroxyphthalimide, 53.3 g (674 mmol) of pyridine and 1100 g of 1,4-dioxane were placed and were stirred at room temperature. To the resulting mixture, 94.8 g (674 mmol) of benzoyl chloride was added dropwise over 1 hour, and the resulting mixture was stirred at room temperature for further 2 hours. Subsequently, 1100 g of pure water was added dropwise over 30 minutes to dissolve by-produced salts and thereby yielded a crystal of the target N-benzoyloxyphthalimide. The mixture was stirred and aged for further 1 hour, the crystal was filtrated using a Nutsche, was rinsed with an appropriate amount of water, was dried at 60° C. under a reduced pressure and thereby yielded 162 g (604 mmol) of N-benzoyloxyphthalimide in a yield of 98.6% on the basis of N-hydroxyphthalimide.

Example 15

In a 500-ml titanium autoclave, 15.36 g (0.113 mol) of p-toluic acid, 0.301 g (1.13 mmol) of N-benzoyloxyphthalimide, 0.112 g (0.45 mmol) of cobalt(II) acetate tetrahydrate, 0.277 g (1.13 mmol) of manganese(II) acetate tetrahydrate and 104 g of acetic acid were placed, the resulting mixture was stirred at 190° C. in an atmosphere of a mixture of oxygen and nitrogen gases (1:1) [4 MPa (gauge pressure)] for 1 hour and thereby yielded terephthalic acid in a yield of 63.2% with a conversion from p-toluic acid of 67.4%. A small amount of 4-carboxybenzaldehyde was by-produced.

Example 16

A mixture of 1.062 g (10 mmol) of ethylbenzene, 0.205 g (1 mmol) of N-acetoxyphthalimide, 0.025 g (0.1 mmol) of cobalt(II) acetate tetrahydrate, 0.025 g (0.1 mmol) of manganese(II) acetate tetrahydrate and 15 ml of acetic acid was stirred at 100° C. in an atmosphere of oxygen gas (1 atm=0.1 MPa) for 8 hours and thereby yielded benzoic acid and acetophenone in yields of 86% and 5% (analyzed by gas chromatography), respectively, with a conversion from ethylbenzene of 99%.

Example 17

A mixture of 1.062 g (10 mmol) of ethylbenzene, 0.205 g (1 mmol) of N-acetoxyphthalimide, 0.025 g (0.1 mmol) of cobalt(II) acetate tetrahydrate, 0.025 g (0.1 mmol) of manganese(II) acetate tetrahydrate and 15 ml of acetic acid was stirred at 130° C. in an atmosphere of air [2 MPa (gauge pressure)] for 8 hours and thereby yielded benzoic acid in a yield of 85% (analyzed by gas chromatography) with a conversion from ethylbenzene of 96%. In this procedure, acetophenone was not produced.

Example 18

A mixture of 1.502 g (10 mmol) of p-tolyl acetate, 0.410 g (2 mmol) of N-acetoxyphthalimide, 0.025 g (0.1 mmol) of cobalt(II) acetate tetrahydrate, 0.025 g (0.1 mmol) of manganese(II) acetate tetrahydrate and 13 g of acetic acid was stirred at 100° C. in an atmosphere of oxygen gas (1 atm=0.1 MPa) for 6 hours and thereby yielded 4-acetoxybenzoic acid in a yield of 77% (analyzed by high performance liquid chromatography) with a conversion from p-tolyl acetate of 86%.

Example 19

A mixture of 20.00 g (215 mmol) of β-picoline, 8.82 g (43 mmol) of N-acetoxyphthalimide, 0.535 g (1 mmol) of cobalt (II) acetate tetrahydrate, 0.527 g (1 mmol) of manganese(II) acetate tetrahydrate and 282.62 g of acetic acid was stirred at 140° C. under flow of air (1 MPa (gauge pressure)] for 3 hours and thereby yielded nicotinic acid in a yield of 58% (analyzed by gas chromatography) with a conversion from β-picoline of 72%.

Example 20

A mixture of 1.202 g (10 mmol) of isopropylbenzene, 0.205 g (1 mmol) of N-acetoxyphthalimide, 0.025 g (0.1 mmol) of cobalt(II) acetate tetrahydrate, 0.025 g (0.1 mmol) of manganese(II) acetate tetrahydrate and 15 ml of acetic acid was stirred at 100° C. in an atmosphere of oxygen gas (1 atm=0.1 MPa) for 8 hours and thereby yielded benzoic acid, acetophenone and 2-phenyl-2-propanol in yields of 30%, 9% and 2% (analyzed by gas chromatography), respectively, with a conversion from isopropylbenzene of 65%.

Example 21

A mixture of 1.202 g (10 mmol) of isopropylbenzene, 0.205 g (1 mmol) of N-acetoxyphthalimide, 0.025 g (0.1 mmol) of cobalt(II) acetate tetrahydrate, 0.025 g (0.1 mmol) of manganese(II) acetate tetrahydrate and 15 ml of acetic acid was stirred at 100° C. in an atmosphere of oxygen gas (1 atm=0.1 MPa) for 2 hours and thereby yielded benzoic acid, acetophenone and 2-phenyl-2-propanol in yields of 5%, 30% and 12% (analyzed by gas chromatography), respectively, with a conversion from isopropylbenzene of 59%.

Example 22

A mixture of 1.202 g (10 mmol) of isopropylbenzene, 0.205 g (1 mmol) of N-acetoxyphthalimide, 0.025 g (0.1 mmol) of cobalt(II) acetate tetrahydrate, 0.025 g (0.1 mmol) of manganese(II) acetate tetrahydrate and 15 ml of acetic acid was stirred at 130° C. in an atmosphere of air (2 MPa) for 8 hours and thereby yielded benzoic acid, acetophenone and 2-phenyl-2-propanol in yields of 52%, 6% and 2% (analyzed by gas chromatography), respectively, with a conversion from isopropylbenzene of 68%.

Example 23

A mixture of 50 mmol of p-xylene, 1 mmol of N-acetoxy-α,α-dimethylsuccinimide (α,α-dimethylsuccinimide acetate), 0.05 mmol of cobalt(II) acetate tetrahydrate and 60 ml of acetic acid was stirred at 150° C. in an atmosphere of oxygen gas (supplied using a balloon) for 4 hours and thereby yielded terephthalic acid, p-toluic acid and p-carboxybenzaldehyde in yields of 89%, 3% and 2%, respectively with a conversion from p-xylene of 95%.

The invention claimed is:

1. A process for producing an organic compound, the process comprising the step of
    allowing (A) a compound capable of forming a radical selected from the group consisting of:
    (A4) compounds each having a carbon-hydrogen bond at the adjacent position to an unsaturated bond selected from the group consisting of toluene; ethylbenzene; isopropylbenzene; benzaldehyde; mixtures of toluene, ethylbenzene, isopropylbenzene and benzaldehyde; p-xylene; p-isopropyltoluene; p-diisopropylbenzene; p-tolualdehyde; p-toluic acid; p-carboxybenzaldehyde; mixtures of p-xylene, p-isopropyltoluene, p-diisopropylbenzene, p-tolualdehyde, p-toluic acid and p-carboxybenzaldehyde; m-xylene; m-tolualdehyde; m-carboxybenzaldehyde; mixtures of m-xylene, m-tolualdehyde and m-carboxybenzaldehyde; pseudocumene; dimethylbenzaldehyde; dimethylbenzoic acid; mixtures of pseudocumene, dimethylbenzaldehyde and dimethylbenzoic acid; durene; trimethylbenzaldehyde; trimethylbenzoic acid; mixtures of durene, trimethylbenzaldehyde and trimethylbenzoic acid; 3-methylquinoline; and β-picoline; and
    (A5) non-aromatic cyclic hydrocarbons selected from the group consisting of 3- to 30-membered cycloalkane ring, and 3- to 30-membered cycloalkene ring; to react with
    (B) a radical scavenging compound which is
    (B4) oxygen-atom-containing reactants selected from the group consisting of oxygen, carbon monoxide, nitrogen oxides, sulfur oxides, nitric acid, nitrous acid, and salts thereof;
    at a reaction temperature of from 0° C. to 300° C., and a reaction pressure of from 0.1 to 10 MPa, in the presence of a catalyst comprising an imide compound having a N-substituted cyclic imide skeleton represented by following Formula (1):

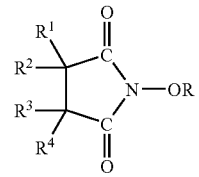

wherein R is a group obtained from an acid selected from the group consisting of carboxylic acids, sulfonic acids, carbonic acid, carbamic acid, sulfuric acid, nitric acid, phosphoric acids and boric acids by eliminating an OH group from the acid; $R^1$, $R^2$, $R^3$ and $R^4$ are the same or different and are each a hydrogen atom, a halogen atom, an alkyl group each having from 1 to 10 carbon atoms, an aryl group, -five or six membered cycloalkyl group, a hydroxyl group, an alkoxy group, a carboxyl group, a substituted oxycarbonyl group which is at least one selected from the group consisting of $C_1$-$C_{20}$ alkoxycarbonyl groups, 3 to 15 membered cycloalkyloxycarbonyl groups, $C_6$-$C_{20}$ aryloxy-carbonyl groups, $C_7$-$C_{21}$ aralkyloxy-carbonyl groups, an acyl group and an acyloxy group, where at least two of $R^1$, $R^2$, $R^3$ and $R^4$ may be combined with each other to form a double bond, an aromatic or non-aromatic ring each having from 5 to 12 members, and where at least one N-substituted cyclic imido group indicated in Formula (1) may further be formed on $R^1$, $R^2$, $R^3$ and $R^4$ or on the double bond, the aromatic or non-aromatic ring formed by at least two of $R^1$, $R^2$, $R^3$ and $R^4$,
    to yield an addition or substitution reaction product between the compound (A) and the compound (B) or a product of a reaction selected from the group consisting of dehydration reaction, cyclization reaction, decarboxylation reaction, rearrangement reaction and isomerization reaction of said addition or substitution reaction product.

2. The process for producing an organic compound according to claim 1, wherein the reaction between the compound (A) capable of forming a radical and the radical scavenging compound (B) is one selected from the group consisting of oxidation reactions, carboxylation reactions, nitration reactions, sulfonation reactions, coupling reactions and combinations thereof.

3. The process for producing an organic compound according to claim 1, comprising the imide compound and a metallic compound in combination.

* * * * *